US010799421B2

(12) United States Patent
Berdahl et al.

(10) Patent No.: US 10,799,421 B2
(45) Date of Patent: Oct. 13, 2020

(54) THERAPEUTIC EYE TREATMENT WITH GASES

(71) Applicant: Equinox Ophthalmic, Inc., Sioux Falls, SD (US)

(72) Inventors: John Berdahl, Sioux Falls, SD (US); George Tsai, Mission Viejo, CA (US)

(73) Assignee: Equinox Ophthalmic, Inc., Sioux Falls, SD (US)

(*) Notice: Subject to any disclaimer, the term of this patent is extended or adjusted under 35 U.S.C. 154(b) by 185 days.

(21) Appl. No.: 16/083,302

(22) PCT Filed: Mar. 8, 2017

(86) PCT No.: PCT/US2017/021240
§ 371 (c)(1),
(2) Date: Sep. 7, 2018

(87) PCT Pub. No.: WO2017/156050
PCT Pub. Date: Sep. 14, 2017

(65) Prior Publication Data
US 2020/0138669 A1 May 7, 2020

Related U.S. Application Data

(60) Provisional application No. 62/305,751, filed on Mar. 9, 2016.

(51) Int. Cl.
*A61F 9/02* (2006.01)
*A61H 35/02* (2006.01)
(Continued)

(52) U.S. Cl.
CPC ............. *A61H 35/02* (2013.01); *A61B 3/102* (2013.01); *A61F 9/0008* (2013.01); *A61F 9/02* (2013.01);
(Continued)

(58) Field of Classification Search
CPC . A61H 35/02; A61B 3/102; A61F 9/00; A61F 9/0008; A61F 9/0026; A61F 9/02; A61F 9/029; A61F 2009/00891
See application file for complete search history.

(56) References Cited

U.S. PATENT DOCUMENTS 3,010,109 A 11/1961 Gray
4,429,956 A 2/1984 Herbert
(Continued)

FOREIGN PATENT DOCUMENTS

DE 19730735 A1 2/1999
EP 2392306 A1 12/2011
(Continued)

OTHER PUBLICATIONS

"Australian Application Serial No. 2017229507, First Examination Report dated Nov. 14, 2019", 3 pgs.
(Continued)

*Primary Examiner* — Catherine L Anderson
*Assistant Examiner* — Lynne Anderson
(74) *Attorney, Agent, or Firm* — Schwegman Lundberg & Woessner, P.A.

(57) ABSTRACT

An apparatus (100) to maintain an environment over an anterior surface of a patient eye can include an enclosure (110) sized and shaped to be seated about the patient eye to form a cavity (112) within the enclosure. The enclosure can be configured to contain a fluid other than ambient air in contact with the patient eye. The apparatus can include a fluid regulator (1209) in communication with the enclosure, where the fluid regulator can be configured to regulate the composition of the fluid contained within the enclosure.

15 Claims, 10 Drawing Sheets

(51) Int. Cl.
  *A61B 3/10* (2006.01)
  *A61F 9/00* (2006.01)
  *A61F 9/008* (2006.01)
(52) U.S. Cl.
  CPC ............... *A61F 2009/00891* (2013.01); *A61H 2201/1238* (2013.01); *A61H 2201/165* (2013.01); *A61H 2205/024* (2013.01)

(56) References Cited

U.S. PATENT DOCUMENTS

| | | | |
|---|---|---|---|
| 4,461,303 A | 7/1984 | Refojo et al. | |
| 4,724,843 A | 2/1988 | Fisher | |
| 4,907,595 A | 3/1990 | Strauss | |
| 4,997,770 A | 3/1991 | Giles et al. | |
| 5,523,808 A | 6/1996 | Kohayakawa | |
| 5,807,357 A | 9/1998 | Kang | |
| 5,927,281 A | 7/1999 | Monteleone et al. | |
| 5,951,477 A | 9/1999 | Ragaluskals et al. | |
| 6,641,264 B1 | 11/2003 | Schhwebel | |
| 6,673,014 B2 | 1/2004 | Badchi et al. | |
| 7,981,095 B2* | 7/2011 | Grenon ................ | A61F 9/0008 604/289 |
| 8,408,204 B2 | 4/2013 | Lurie | |
| 8,936,021 B2 | 1/2015 | Collins, Jr. | |
| 9,125,724 B2 | 9/2015 | Berdahl et al. | |
| 9,445,767 B2 | 9/2016 | Abreu | |
| 2002/0124843 A1 | 9/2002 | Skiba et al. | |
| 2007/0265505 A1 | 11/2007 | Guillon et al. | |
| 2011/0022010 A1 | 1/2011 | Grenon et al. | |
| 2012/0222201 A1 | 9/2012 | Dondero | |
| 2013/0150699 A1 | 6/2013 | Ostermeier et al. | |
| 2013/0238015 A1 | 9/2013 | Berdahl et al. | |
| 2013/0274638 A1 | 10/2013 | Jennings et al. | |
| 2014/0275935 A1 | 9/2014 | Walsh et al. | |
| 2015/0313761 A1 | 11/2015 | Berdahl et al. | |

FOREIGN PATENT DOCUMENTS

| | | |
|---|---|---|
| EP | 3426219 B1 | 2/2020 |
| JP | 2019198742 A | 11/2019 |
| WO | WO-2017156050 A1 | 9/2017 |
| WO | WO-2018174835 A1 | 9/2018 |

OTHER PUBLICATIONS

"Australian Application Serial No. 2017229507, Response filed Jan. 17, 2020 to First Examination Report dated Nov. 14, 2019", 22 pgs.
"Canadian Application Serial No. 3,017,154, Office Action dated Oct. 2, 2019", 4 pgs.
"Indian Application Serial No. 201817038048, First Examiners Report dated Jan. 14, 2020", w/ English Translation, 7 pgs.
"Korean Application Serial No. 10-2018-7029058, Notice of Preliminary Rejection dated Feb. 14, 2020", w/ English Translation, 5 pgs.
"Canadian Application Serial No. 3,017,154, Response filed Apr. 2, 2020 to Office Action dated Oct. 2, 2019", 16 pgs.
"Indian Application Serial No. 201817038048, Response filed Apr. 15, 2020 to First Examiners Report dated Jan. 14, 2020", 61 pgs.
"Japanese Application Serial No. 2019-156790, Voluntary Amendment filed Mar. 6, 2020", w/ English Claims, 5 pgs.
"Korean Application Serial No. 10-2018-7029058, Response filed Mar. 31, 2020 to Notice of Preliminary Rejection dated Feb. 14, 2020", w/ English Claims, 12 pgs.
"European Application Serial No. 17712612.5, Response Filed Oct. 16, 2018 to Communication pursuant to Rules 161(1) and 162 EPC dated Oct. 16, 2018", w/ English Claims, 12 pgs.
"Indian Application Serial No. 201817038048, Voluntary Amendment filed Dec. 7, 2018", w/English Claims, 12 pgs.
"International Application Serial No. PCT/US2017/021240, International Preliminary Report on Patentability dated Sep. 20, 2018", 8 pgs.

"Cataract Surgery to Lower Intraocular Pressure", Middle East African Journal of Ophthalmology, 16 (3), (Sep. 2009), 1-5.
"Drug Absorption and Disposition in the Eye", Review on Ocular Drug Delivery / Pharma Tutor, [Online]. Retrieved from the Internet: <URL: http://www.pharmatutor.org/articles/reviewonoculardrugdelivery?page=0,3, (Sep. 19, 2015), 1-7.
"Eyemate", IOP GmbH, [Online]. Retrieved from the Internet: <URL: http://www.implandata/com/eyemate.html>, (Accessed Oct. 9, 2015), 2 pgs.
"International Application Serial No. PCT/US2017/021240, International Search Report dated Jun. 20, 2017", 8 pgs.
"International Application Serial No. PCT/US2017/021240, Written Opinion dated Jun. 20, 2017", 6 pgs.
"Non-Invasive Oxygen Sensors", [Online]. Retrieved from the Internet: <URL: http://www.presens.de/fileadmin/user_upload/products/Sensor_Probes/Noninvasive_oxygen_sensors/150205_SP-NonInvOx-15-01_w.pdf, (Accessed Mar. 8, 2016), 4 pgs.
Alexander, David J., et al., "Risk of Spaceflight-Induced Intracranial Hypertension and Vision Alterations", Evidence Report—Version 1.0, (Jul. 12, 2012), 109 pgs.
Allin, David, et al., "Laboratory Testing of the Pressio Intracranial Pressure Monitor", Neurosurgery, vol. 62, vol. 5, [Online]. Retrieved from the Internet: <URL: www.neurosurgery-online.com, (May 2008), 1158-1161.
Araci, Ismail E., "An implantable microfuidic device for self-monitoring of intraocular pressure", nature medicine, vol. 20, No. 9—Technical Reports, (Sep. 2014), 1074-1080.
Berdahl, et al., "Cerebrospinal fluid pressure is decreased in primary open-angle glaucoma", Ophthalmology 115(5), (May 2008), 763-768.
Berdahl, John P., et al., "Body Mass Index Has a Linear Relationship with Cerebrospinal Fluid Pressure", IOVS, vol. 53, No. 3, (Mar. 2012), 1422-1427.
Berdahl, John P., et al., "Intracranial pressure and glaucoma", Current Opinion in Ophthalmology 21-, (2010), 106-111.
Berdahl, John P., et al., "Intracranial Pressure in Primary Open Angle Glaucoma, Normal Tension Glaucoma, and Ocluar Hypertension: A Case-Control Study", IOVS, vol. 49, No. 12, (Dec. 2008), 5412-5418.
Berdahl, John P., "Recovery of Corneal Hysteresis after Reduction of Intraocular Pressure in Chronic Primary Angle-Closure Glaucoma", American Journal of Ophthalmology—Correspondence, (Oct. 2009), 623-624.
Berdahl, John P., "Systemic Parameters Associated With Cerebrospinal Fluid Pressure", J Glaucoma, vol. 22, No. 5, Suppl 1, [Online]. Retrieved from the Internet: <URL: www.glaucomajournal.com, (Jul. 2013), S17-S18.
Berdahl, John P., "The translaminar pressure gradient in sustained zero gravity, idiopathic inracranial hypertension and glaucoma", Medical Hypotheses 79, (2012), 719-724.
Ersanli, D/, et al., "The effect of hyperbaric oxygen on intraocular pressure", UHM vol. 33, No. 1, (2006), 1-4.
Fleischman, David, et al., "Cerebrospinal Fluid Pressure Decreases with Older Age", PLOS One, vol. 7, Issue 12, [Online]. Retrieved from the Internet: <URL: www.plosone.org, (Dec. 2012), 1-9.
Fleischman, David, et al., "Increasing intraocular pressure as treatment for papilledema", Experimental Eye Research 115, (2013), 278.
Gallin-Cohen, Pamela F., et al., "Oxygen lowers intraocular pressure", Invest. Ophthalmol. Vis. Sci, (Jan. 1980), 43-48.
Guadana, Ripal, et al., "Ocular Drug Delivery", The AAPS Journal, vol. 12, No. 3, (Sep. 2010), 348-360.
Hayreh, Sohan Singh, "Cerebrospinal fluid pressure and glaucomatous optic disc cupping (response to Berdahl and colleagues)", Graefes Arch Clin Exp Opthalmol, 247, (2009), 1291-1294.
Hillen, Mark, "In Practice (VIIP: A Space Odyssey)", The Ophthalmologist , vol. 11, (Sep. 2014), 6 pgs.
Kwon, Oh Seok, et al., "Flexible FET-Type VEGF Aptasensor Based on Nitrogen-Doped Graphene Converted from Conducting Polymer", ACS Nano, vol. 6, No. 2, (2012), 1486-1493.
Lalwani, K, et al., "The effect of nitrous oxide on intra-ocular pressure in healthy adults", Anaesthesia 2012, 67, (2012), 256-260.

(56) References Cited

OTHER PUBLICATIONS

Melki, Samir, et al., "An implantable Intraocular Pressure Transducer Initial Safety Outcomes", JAMA Ophthalmology, [Online]. Retrieved from the Internet: <URL: http://archopht.jamanetwork.com/, (Jun. 26, 2014), E1-E5.

Muenster, Stefan, et al., "The Ability of Nitric Oxide to Lower Intraocular Pressure is Dependent on Guanylyl Cyclase", Investigative Ophthalmology & Visual Science, vol. 58, No. 11, (Sep. 2017), 4826-4835.

Niwa, Yoshiaki, et al., "A New System to Supply Carbon Dioxide Safely to Glaucoma Patients", Jpn J Ophthalmol 43, (1999), 16-19.

Paschalis, Eleftherios, et al., "Reliable intraocular pressure meausrement using automated radio-wave telemetry", Clinical Ophthalmology 2014: 8, (2014), 177-185.

Patane, Michael, et al., "Ocular Iontophoresis for Drug Delvery", Retina Today, (Mar. 2011), 64-66.

Samuel, J. R., et al., "Effect 0f carbon dioxide on the intraocular pressure in man during general anaethesia", Brit. J. Ophthal 58,62, [Online]. Retrieved from the Internet: <URL: http://bjo.bmj.com/, (1974), 62-67.

Singh, Daljit, "Fuchs Endothelial Dystrophy Treatment & Management—Medical Care", (Aug. 19, 2014), 3 pgs.

Song, Sniping, et al., "Aptamer-based biosensors", Trends in Analytical Chemistry, vol. 27, No. 2, (2008), 108-117.

Yeoh, Ronald, "Hydrorupture of the posterior capsule in femtosecond-laser cataract surgery", J Cataract Refract Surg, vol. 38, (Apr. 2012), 730-731.

Yoo, Eun-Hyung, et al., "Glucose Biosensors: An Overview of Use in Clinical Practice", Sensors 10, (2010), 4558-4576.

\* cited by examiner

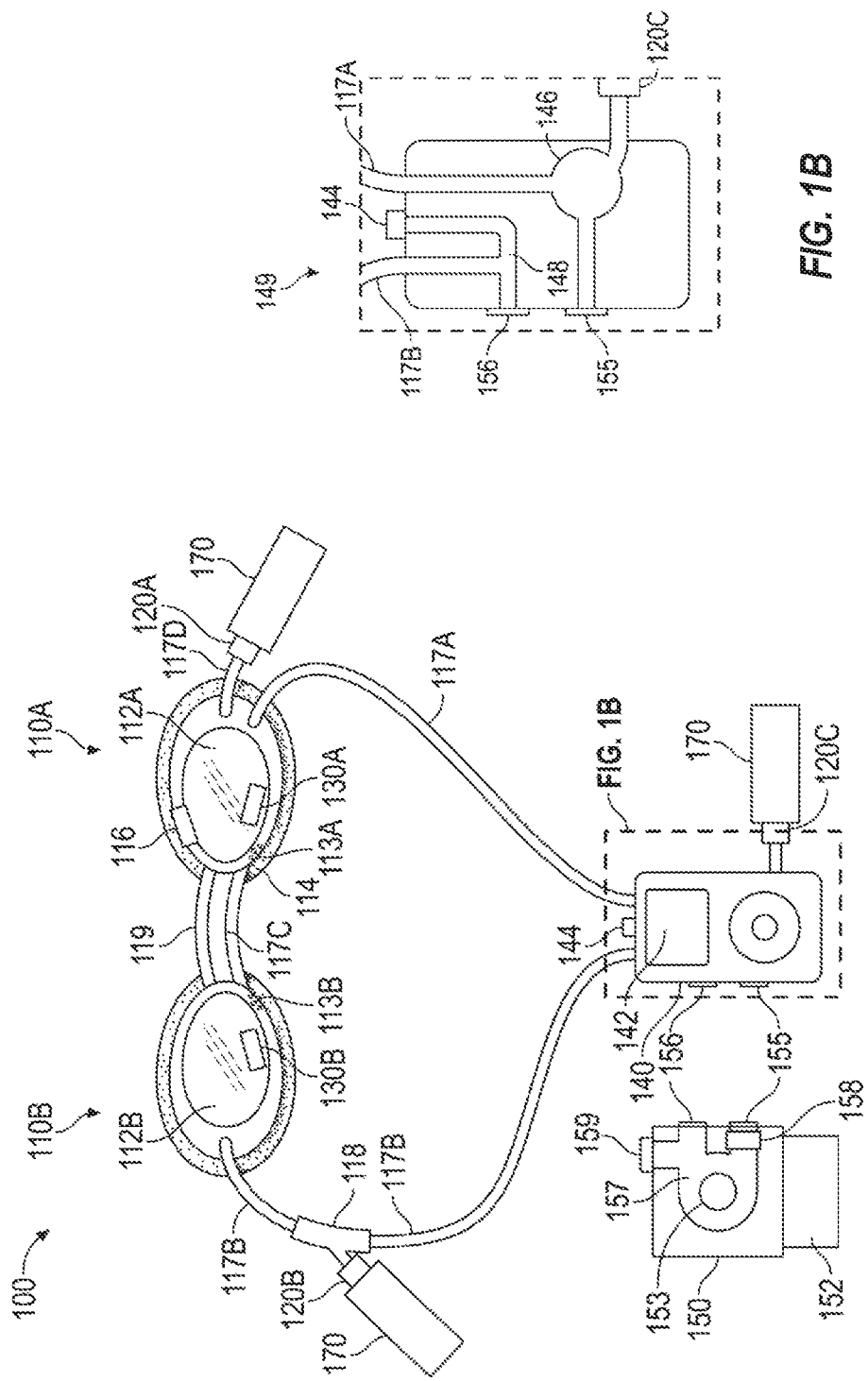

THERAPEUTIC EYE TREATMENT WITH GASES

CLAIM OF PRIORITY

This patent application is a U.S. National Stage Application under 35 U.S.C. 371 from International Application No. PCT/US2017/021240, filed Mar. 8, 2017, which claims the benefit of priority of U.S. Provisional Patent Application Ser. No. 62/305,751, to John Berdahl entitled "Therapeutic Eye Treatment with Gases," filed on Mar. 9, 2016 each of which are hereby incorporated by reference in their entirety.

BACKGROUND

Patient compliance in applying therapeutic substances to an eye is important in treating diseases of the eye, such as glaucoma. Topical medications, such as eye drops, can drain quickly from the eye thereby minimizing contact time with absorbing surfaces, such as the cornea, sclera, and conjunctiva.

Kang U.S. Pat. No. 5,807,357 mentions a compact nebulizer for treating the eyes including a goggles unit having an air hole and at least one air chamber communicating with the air hole and fitting over the user's eyes. A plurality of exhausting holes are made at the goggle unit for exhaust air.

Skiba U.S. Patent Application No, 2002/0124843 mentions a mask worn around the eyes with one or more fog outlets an atomizer to nebulize medicine into a fog such that the fog discharges from the fog outlets to delivery medicine to one or more eyes.

Guillon U.S. Patent Application No. 2007/0265505 mentions an eye enclosure adapted to provide an enclosed area about the eyes of the user, a means for retaining the eye enclosure in position, and means for supplying dry air to the eye enclosure.

OVERVIEW

The present inventors have recognized, among other things, that there is a need in the art for methods and devices that will allow for the delivery of therapeutic gases, such as carbon dioxide ($CO_2$), oxygen ($O_2$), nitric oxide (NO), ozone ($O_3$), nitrogen, hydrocarbons including fluorocarbons and perfluorocarbons, sulfur hexafluoride, and combinations of therapeutic substances, such as a mixture of nitric oxide and oxygen, including a mixture of 50% nitric oxide and 50% oxygen, a mixture of helium and oxygen, also known as heliox, and Medical Air, through the surfaces of the eye, such as the corneal, scleral, and conjunctival surfaces, over an extended period time. New therapeutic techniques, such as applying a therapeutic force to the anterior portion of the eye, can supplement pharmacological regimens. Enhanced patient outcomes can be realized by combining therapeutic substances with new techniques.

This document describes, among other things, methods and apparatuses for introducing gaseous fluids to an eye to treat an eye condition. The method can include providing an enclosure. The enclosure can be sized and shaped to be seated about an eye and form a cavity within the enclosure. A gaseous fluid other than ambient air can be introduced into the cavity, such as to provide therapy to the eye. The gaseous fluid can include a specified non-ambient concentration of at least one of carbon dioxide ($CO_2$), oxygen ($O_2$), or nitric oxide ($N_2O$).

An overview of certain non-limiting aspects of the present subject matter is provided below.

Aspect 1 can include or use subject matter (such as an apparatus, a system, a device, a method, a means for performing acts, or a device readable medium including instructions that, when performed by the device, can cause the device to perform acts), such as an apparatus to maintain an environment over an anterior surface of a patient eye. An enclosure sized and shaped to be seated about the patient eye can form a cavity within the enclosure. The enclosure can be configured to contain a fluid other than ambient air such as the fluid can be in contact with the patient eye. A fluid regulator can be in communication with the enclosure. The fluid regulator can be configured to regulate the composition of the fluid contained within the enclosure.

Aspect 2 can include or use, or can optionally be combined with the subject matter of Aspect 1 to optionally include or use the enclosure configured to maintain a differential fluid pressure between the cavity and the surrounding environment and the fluid regulator is configured to regulate the differential pressure of the fluid contained within the enclosure.

Aspect 3 can include or use, or can optionally be combined with the subject matter of one or any combination of Aspects 1 or 2 to optionally include or use a fluid that can include a gaseous fluid.

Aspect 4 can include or use, or can optionally be combined with the subject matter of one or any combination of Aspects 1 through 3 to optionally include or use the gaseous fluid wherein the gaseous fluid includes a specified non-ambient percentage of at least one of carbon dioxide ($CO_2$), oxygen ($O_2$), or nitric oxide (NO).

Aspect 5 can include or use, or can optionally be combined with the subject matter of one or any combination of Aspects 1 through 4 to optionally include or use the gaseous fluid wherein the gaseous fluid includes a specified non-ambient percentage of carbon dioxide ($CO_2$).

Aspect 6 can include or use, or can optionally be combined with the subject matter of one or any combination of Aspects 1 through 5 to optionally include or use the gaseous fluid wherein the gaseous fluid includes a specified non-ambient percentage of oxygen ($O_2$).

Aspect 7 can include or use, or can optionally be combined with the subject matter of one or any combination of Aspects 1 through 6 to optionally include or use the gaseous fluid wherein the gaseous fluid includes a specified non-ambient percentage of nitric oxide (NO).

Aspect 8 can include or use, or can optionally be combined with the subject matter of one or any combination of Aspects 1 through 7 to optionally include or use a sensor configured to detect at least one of an indication of the eye or an indication of a parameter of an environment within the cavity.

Aspect 9 can include or use, or can optionally be combined with the subject matter of one or any combination of Aspects 1 through 8 to optionally include or use the sensor wherein the sensor includes an optical coherence tomography (OCT) system.

Aspect 10 can include or use, or can optionally be combined with the subject matter of one or any combination of Aspects 1 through 9 to optionally include or use the sensor wherein the sensor includes a non-contact blood vessel characteristic detector.

Aspect 11 can include or use, or can optionally be combined with the subject matter of one or any combination of Aspects 1 through 10 to optionally include or use the sensor wherein the sensor includes a quartz crystal nanobalance sensor.

Aspect 12 can include or use, or can optionally be combined with the subject matter of one or any combination of Aspects 1 through 11 to optionally include or use the sensor wherein the sensor includes a non-invasive optical oxygen sensor.

Aspect 13 can include or use, or can optionally be combined with the subject matter of one or any combination of Aspects 1 through 12 to optionally include or use the sensor wherein the sensor includes a salinity sensor.

Aspect 14 can include or use, or can optionally be combined with the subject matter of one or any combination of Aspects 1 through 13 to optionally include or use the sensor wherein the sensor includes an aptamer-based sensor.

Aspect 15 can include or use, or can optionally be combined with the subject matter of one or any combination of Aspects 1 through 14 to optionally include or use a processor module in communication with at least one of the fluid regulator or a sensor.

Aspect 16 can include or use, or can optionally be combined with the subject matter of one or any combination of Aspects 1 through 15 to optionally include or use the processor wherein the processor module is in communication with the fluid regulator.

Aspect 17 can include or use, or can optionally be combined with the subject matter of one or any combination of Aspects 1 through 16 to optionally include or use the processor wherein the processor unit is in communication with the sensor.

Aspect 18 can include or use, or can optionally be combined with the subject matter of one or any combination of Aspects 1 through 17 to optionally include or use a pump in communication with at least one of the processor or the enclosure.

Aspect 19 can include or use, or can optionally be combined with the subject matter of one or any combination of Aspects 1 through 18 to optionally include or use the pump wherein the pump is in communication with the processor.

Aspect 20 can include or use, or can optionally be combined with the subject matter of one or any combination of Aspects 1 through 19 to optionally include or use the pump wherein the pump is in communication with the enclosure.

Aspect 21 can include or use, or can optionally be combined with the subject matter of one or any combination of Aspects 1 through 20 to optionally include or use the pump wherein the pump is a vacuum pump.

Aspect 22 can include or use subject matter (such as an apparatus, a system, a device, a method, a means for performing acts, or a device readable medium including instructions that, when performed by the device, can cause the device to perform acts), or can optionally be combined with the subject matter of one or any combination of Aspects 1 through 21 to optionally include or use or provide an enclosure that is sized and shaped to be seated about the patient eye to form a cavity within the enclosure. At the enclosure, a fluid other than ambient air can be provided to the cavity such as to treat an eye condition.

Aspect 23 can include or use, or can optionally be combined with the subject matter of one or any combination of Aspects 1 through 22 to optionally include or use providing a fluid to maintain a differential fluid pressure between the cavity and the surrounding environment.

Aspect 24 can include or use, or can optionally be combined with the subject matter of one or any combination of Aspects 1 through 23 to optionally include or use sensing an indication of the fluid other than ambient air in the cavity.

Aspect 25 can include or use, or can optionally be combined with the subject matter of one or any combination of Aspects 1 through 24 to optionally include or use sensing wherein sensing an indication includes sensing an indication of at least one of fluid pressure, fluid partial pressure, fluid concentration, or fluid humidity.

Aspect 26 can include or use, or can optionally be combined with the subject matter of one or any combination of Aspects 1 through 25 to optionally include or use sensing Wherein sensing an indication of fluid partial pressure includes sensing a fluid partial pressure of at least one of carbon dioxide ($CO_2$), oxygen ($O_2$), nitric oxide (NO), ketones, glucose, oxygen levels, dissolved salts, or vascular endothelial growth factor.

Aspect 27 can include or use, or can optionally be combined with the subject matter of one or any combination of Aspects 1 through 26 to optionally include or use sensing Wherein sensing an indication of fluid concentration includes sensing a concentration of at least one of carbon dioxide ($CO_2$), oxygen ($O_2$), nitric oxide (NO), ketones, glucose, oxygen levels, dissolved salts, or vascular endothelial growth factor.

Aspect 28 can include or use, or can optionally be combined with the subject matter of one or any combination of Aspects 1 through 27 to optionally include or use sensing an indication of the patient eye.

Aspect 29 can include or use, or can optionally be combined with the subject matter of one or any combination of Aspects 1 through 28 to optionally include or use sensing wherein sensing an indication of the patient eye includes sensing an indication of at least one of an indication of intraocular pressure, an indication of translaminar pressure, or an indication of intracranial pressure.

Aspect 30 can include or use, or can optionally be combined with the subject matter of one or any combination of Aspects 1 through 29 to optionally include or use sensing wherein sensing an indication of translaminar pressure includes sensing an indication of at least one of a deflection of the lamina cribrosa, a change in deflection of the lamina cribrosa, or a change in a blood vessel characteristic.

Aspect 31 can include or use, or can optionally be combined with the subject matter of one or any combination of Aspects 1 through 30 to optionally include or use adjusting an indication of the fluid other than ambient air.

Aspect 32 can include or use, or can optionally be combined with the subject matter of one or any combination of Aspects 1 through 31 to optionally include or use adjusting wherein adjusting an indication includes adjusting an indication of at least one of fluid pressure, fluid partial pressure, fluid concentration, or fluid humidity.

Aspect 33 can include or use, or can optionally be combined with the subject matter of one or any combination of Aspects 1 through 32 to optionally include or use or provide a gaseous fluid including a gaseous fluid with a specified non-ambient concentration of at least one of carbon dioxide ($CO_2$), oxygen ($O_2$), nitric oxide (NO), ozone ($O_3$), nitrogen, hydrocarbons, helium, sulfur hexafluoride, Medical Air, or water vapor.

Aspect 34 can include or use, or can optionally be combined with the subject matter of one or any combination of Aspects 1 through 33 to optionally include or use receiving a patient with an eye condition that includes at least one of Fuchs' dystrophy, glaucoma, dry eye, diabetic retinopathy, cataract, venous and arterial occlusive diseases, macular degeneration, diseases of the cornea, endothelium, and epithelium, diseases of the retinal vasculature, diseases of the retinal pigmented epithelium, corneal infections, or other infections of the eye.

Aspect 35 can include or use, or can optionally be combined with the subject matter of one or any combination of Aspects 1 through 34 to optionally include or use providing wherein providing a fluid includes providing a gaseous fluid with a partial pressure between 30 percent and 100 percent oxygen ($O_2$).

Aspect 36 can include or use, or can optionally be combined with the subject matter of one or any combination of Aspects 1 through 35 to optionally include or use a gaseous fluid wherein the gaseous fluid includes a specified concentration of carbon dioxide ($CO_2$).

Aspect 37 can include or use, or can optionally be combined with the subject matter of one or any combination of Aspects 1 through 36 to optionally include or use a gaseous fluid wherein the gaseous fluid includes a specified concentration of nitric oxide (NO).

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIG. 1A shows an example of an apparatus, such as for introducing therapeutic gases to an eye.

FIG. 1B shows an example of a manifold, such as attached to the apparatus of FIG. 1A.

DETAILED DESCRIPTION

Figure 2A:
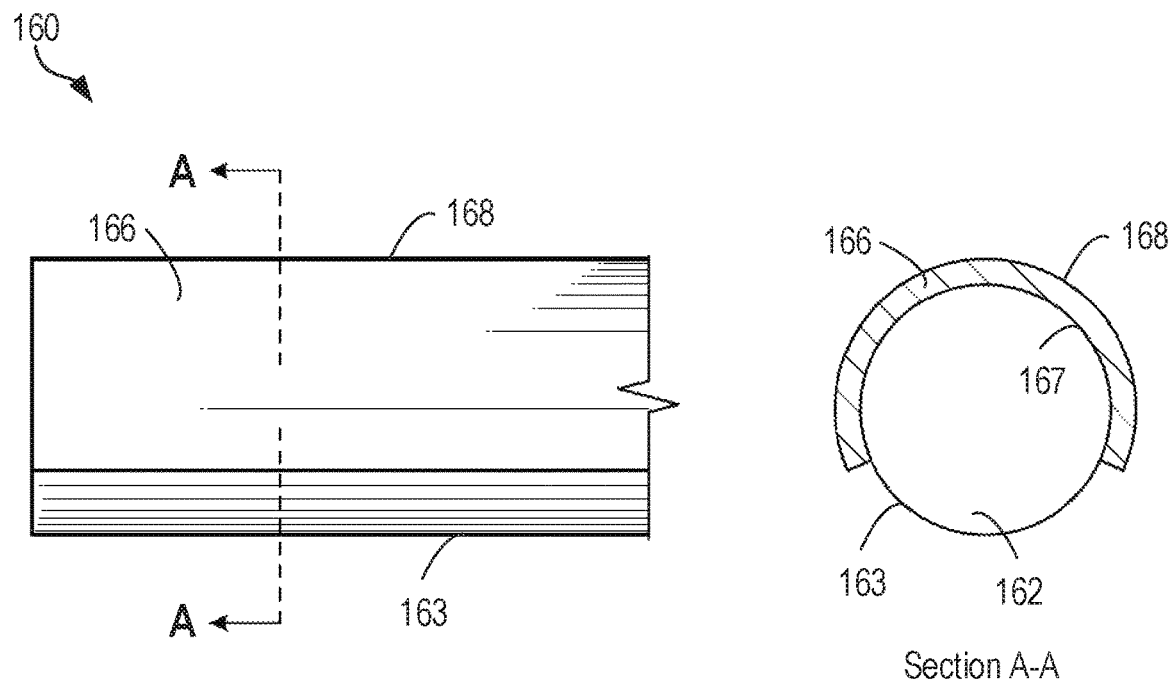
FIG. 2A shows a first example of a wicking gasket.

This document describes examples of devices and methods for establishing, maintaining, and controlling a therapeutic environment in contact with a patient eye, such as to provide for the treatment of eye conditions with different treatment modalities simultaneously.

In an example, the present devices can include a goggle, such as a pair of goggles, located over the eye of the patient. The goggle can include an enclosure that defines a cavity, such as the cavity between the interior surface of the enclosure and the patient when the enclosure can be located over the eye of the patient, and a fluid regulator, such as to control delivery of fluid including a fluid other than ambient air to the cavity. An environment, such as a therapeutic environment, can be established within the cavity, such as to treat an eye condition associated with the patient eye. The eye condition to be treated can dictate the therapeutic environment required to be maintained in the cavity. In an example, the therapeutic environment within the cavity can be characterized with system parameters.

In an example, the present devices can include a goggle, a fluid regulator, a sensor in proximity to the goggle, a pump in fluidic communication with the goggle, and a processing module in electrical communication with at least one of the fluid regulator, the sensor, or the pump. An environment, such as a therapeutic environment, can be established, maintained, and controlled within the cavity, such as with a closed-loop controller, to treat an eye condition associated with the patient eye.

A first system parameter of the therapeutic environment can include the composition of the fluid in the cavity, such as the composition of the constituent fluids that can form the therapeutic environment. As the therapeutic environment can be in contact with the surface of the eye, the partial pressure of one or more constituent fluids in the cavity can be used to treat an eye condition, such as through absorption of the one or more constituent fluids through the anterior portion of the eye. In an example, swelling of the cornea, such as associated with Fuchs dystrophy, can be treated by exposing the cornea to a therapeutic environment, such as a therapeutic environment with a non-ambient volume concentration of gaseous oxygen (O2). In an example, the therapeutic environment in the cavity 112 can be applied to the eye at an ambient pressure, such as the pressure in the cavity 112 can be equal to or approximately equal to the pressure of the environment surrounding the enclosure 110.

A second system parameter of the therapeutic environment can include the gauge pressure of the therapeutic environment, such as the differential pressure between the therapeutic environment in the cavity and the ambient surroundings. The gauge pressure of the fluid in the cavity can be used to treat an eye condition, such as by applying a mechanical force to the eye. In an example, symptoms of glaucoma, such as elevated intraocular or translaminar pressure, can be treated by applying a negative gauge pressure to the cavity, such as to allow a volume expansion of the eye to reduce intraocular pressure or equalize translaminar pressure of the patient eye.

In an example, a combination of system parameters, such as gauge pressure and fluid composition, can be used to improve the treatment of an eye condition, such as by simultaneously treating the eye condition with more than one treatment modality. In an example, macular edema, such as due to fluid accumulation in the macula of the eye, can be treated in a therapeutic environment with a combination of positive gauge pressure, such as to equalize the translaminar pressure difference in the eye to reduce macular swelling, and with a therapeutic fluid, such as with a substance known to increase vasodilation including a non-ambient volume concentration of at least one of carbon dioxide ($CO_2$) or nitric oxide (NO).

FIG. 1A shows an example of an apparatus 100, such as for forming a therapeutic environment over an eye. The apparatus 100 can include an enclosure 110, such as a first enclosure 110A and a second enclosure 110B, a fluid regulator 120, a sensor 130, a processor module 140, and a pump 150, such as in communication with the processor module 140.

The enclosure 110 can be sized and shaped to surround a patient eye and be spaced from the eye, such as without contacting the eye. The enclosure 110 can define an enclosed cavity 112 when the enclosure 110 is placed against the patient, such as a cavity 112 between an inner surface of the enclosure 110 and the patient eye. The enclosure 110 can be constructed from an optically transparent material such as to allow a patient to see outward through the enclosure 110 or to allow observation of the eye inward through the enclosure 110. The inner surface of the enclosure 110 can be treated, such as with an anti-fog coating to prevent condensation from obscuring the view of the patient. The enclosure 110 can include a hole 113, such as a plurality of holes 113, to allow for drainage of condensate from the cavity 112. In an example, the diameter of the hole 113 can vary, such as in a range of from about 1 mm to about 10 mm. The enclosure 110 can include a gasket 114, such as a gasket located around at least a portion of a perimeter of the enclosure 110. The enclosure 110 can be positioned over the eye, such as the gasket 114 can be located against the skin of the patient, such as to form a hermetic seal between the enclosure 110 and the skin, to isolate the cavity 112 from the surrounding environment. In an example the gasket 114 can include a wicking gasket 160, such as a gasket that can receive and retain a fluid, such as a condensate, that can appear in the cavity 112 during the operation of the apparatus 100.

FIG. 2A shows a first example of a wicking gasket 160. The wicking gasket 160 can include a wicking core 162 with a first surface 163 and a core cover 166 with an interior surface 167 and an exterior surface 168. The wicking gasket 162 and core cover 166 can contact the skin, such as at least a portion of the first surface 163 and the exterior surface 168 can contact the skin, to absorb condensate, such as water, sweat, or other liquid fluids in the cavity 112. Removing excess condensate from the cavity 112 can improve patient comfort during use of the apparatus 100.

The wicking core 162 can be constructed from an absorbing material, such as a material that can use capillary action to transfer fluid from a first location to a second location, such as expanded polytetrafluoroethylene (or PTFE). The core cover 166 can be constructed from a porous material, such as a material with a porosity selected to achieve a specified migration rate of condensate through the wicking gasket 160, the material selected to minimize discomfort caused by the enclosure 110 when placed against the skin of the patient, such as for extended time periods. In an example, the core cover 166, such as the interior surface 167, can encapsulate the wicking core 162, such as at least a specified portion or surface area percentage of the first surface 163.

Figure 2B:
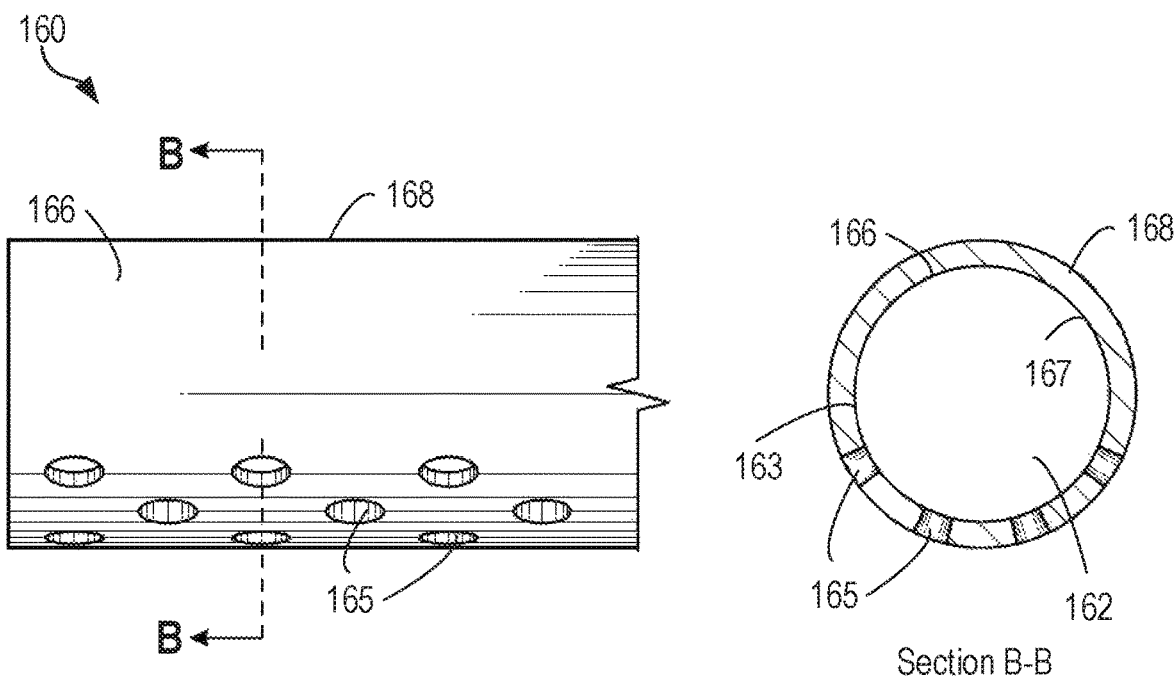
FIG. 2B shows a second example of a wicking gasket.

FIG. 2B shows a second example of a wicking gasket 160. The core cover 166 can substantially encapsulate the wicking core 162 and can include a receiving hole 165, such as a plurality of receiving holes 165, extending through the core cover 166, such as from the interior surface 167 to the exterior surface 168. The receiving hole 16:5 can place the wicking core 162 in communication with the cavity 112, such as condensate can flow from the cavity 112 through the receiving hole 165 to the wicking core 162, to remove condensate from the cavity 112.

Figure 3:
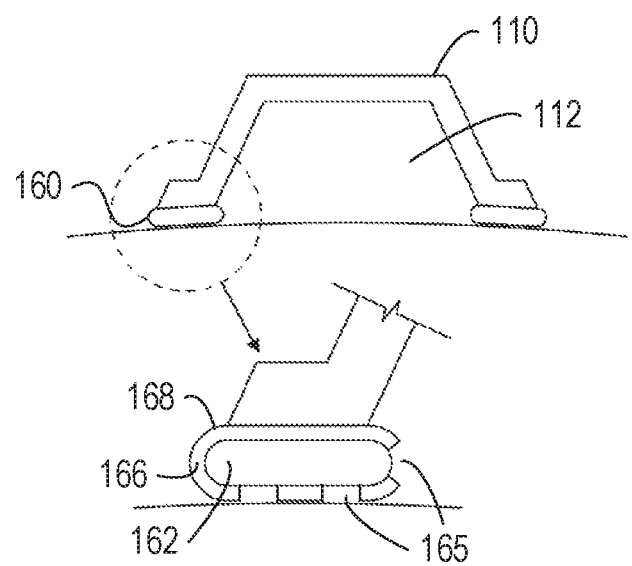
FIG. 3 shows a cross-section of an example wicking gasket attached to an enclosure.

FIG. 3 shows a cross-section of an example wicking gasket 160 attached to an enclosure 110, such as the perimeter of the enclosure 110. In operation, the wicking gasket 160 can be located against a patient, such as in contact with the skin of the patient, to separate the cavity 112 from the surrounding environment. The wicking core 162 can be in communication with the cavity 112 to absorb accumulated condensate, such as through the receiving hole 165. In an example, absorbed condensate can migrate through the wicking core 162 and the core cover 166, such as to evaporate from the exterior surface 168 exposed to the surrounding environment.

Figure 4:
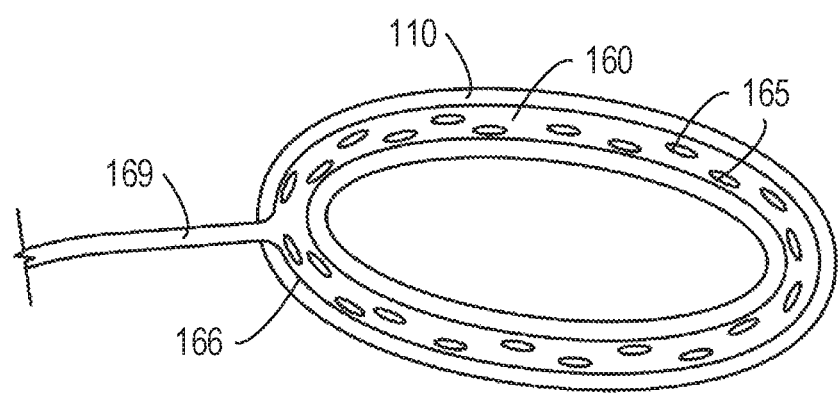
FIG. 4 shows a bottom view of an example wicking gasket with a suction tube, the wicking gasket attached to an enclosure.

FIG. 4 shows a bottom view of an example wicking gasket 160 with a suction tube 169, the wicking gasket 160 attached to an enclosure 110. In an example, the suction tube 169 can be attached to the core cover 166 and the lumen of the suction tube 169 can be in communication with the wicking core 162. A negative gauge pressure can be generated in the lumen of the suction tube 169 and applied to a surface of the wicking core 162, such as to cause migration of condensate absorbed by the wicking core 162 through the wicking core 162 to the suction tube 169, such as to remove the condensate from the cavity 112. Negative gauge pressure can be generated by a condensate pump attached to the suction tube 169. In an example, the condensate pump can include a pump separate from the apparatus 100, such as a standalone pump that can generate a vacuum, and a pump included in the apparatus 100, such as the pump 150.

The enclosure 110 can be secured to the patient to locate the enclosure 110 over the eye of the patient, such as with an adjustable strap attached to the enclosure 110, the adjustable strap substantially encircling the head.

The enclosure 110 can maintain a differential fluid pressure, such as a gauge pressure, between the cavity 112 and another pressure region, such as the atmosphere surrounding the enclosure 110. The fluid contained within the cavity 112 can exert a pressure on an anterior surface of the eye, such as to apply a therapeutic force to the eye to treat an eye condition. In an example, a positive gauge pressure can exert a therapeutic compressive force on the eye, such as to increase the intraocular pressure (or IOP) of the eye. In an example, a negative gauge pressure can exert a therapeutic vacuum force on the eye, such as to decrease the IOP of the eye.

The cavity 112 can contain a fluid, such as a therapeutic fluid including a fluid other than ambient air, in contact with the eye. The therapeutic fluid can be absorbed by the eye, such as through the anterior surface of the eye, to treat an eye condition. In an example, the therapeutic fluid can be composed of a medicinal fluid, such as a liquid fluid and a gaseous fluid.

A therapeutic fluid can include a medicinal fluid, such as a liquid fluid including a miscible solution, such as an aqueous solution, and a colloidal suspension. Aqueous solutions can include therapeutic substances, such as medications and vitamins, dissolved in water. In an example, medications can include anesthetic drops, antibiotics, or substances to diagnose and treat glaucoma. In an example, the therapeutic fluid can be aerosolized, such as to create a mist or fog of therapeutic fluid.

A therapeutic fluid can include a medicinal fluid, such as a gaseous fluid including a therapeutic gas. A therapeutic gas can include carbon dioxide ($CO_2$), oxygen ($O_2$), nitric oxide (NO), ozone ($O_3$), nitrogen, helium (He), hydrocarbons including fluorocarbons and perfluorocarbons, sulfur hexafluoride, and combinations of therapeutic gases. In an example, a therapeutic gas can include a mixture of at least one of carbon dioxide, oxygen, or nitric oxide. In an example, a therapeutic gas can include a mixture of nitric oxide and oxygen including a mixture of 50% nitric oxide and 50% oxygen, a mixture of helium and oxygen (also known as heliox), and Medical Air, such as Medical Grade Air USP. In an example, a combination of therapeutic gases can include a mixture of nitric oxide and oxygen, such as a mixture of 50% nitric oxide and 50% oxygen including gases from The BOC Group plc under the tradename ENTONOX. In an example, a mixture can include a mixture of helium and oxygen, such as a mixture of 21% oxygen and 79% helium, also known as heliox.

The combination of applying a therapeutic fluid, such as other than ambient air, to a cavity 112 at a gauge pressure, such as to generate a therapeutic force against the eye, can allow for simultaneous, multi-modal therapeutic treatment of the patient eye. In an example, an eye condition, such as macular edema or fluid accumulation in the macula of the eye, treated with the combination of a therapeutic fluid, such as a vasodilator including a non-ambient volume concentration of at least one of carbon dioxide ($CO_2$) or nitric oxide (NO) to improve circulation and elimination of fluid from the macula, applied at a gauge pressure in the cavity 112, such as a positive gauge pressure to apply a compressive force to the eye with the therapeutic fluid to reduce macular swelling, can improve the treatment of the eye condition and patient quality of life.

The enclosure 110 can include a port 116, such as a port 116 located in a surface of the enclosure 110. The port 116 can include a septum, such as a septum resealable to needle punctures, to allow for the introduction of instruments into the cavity 112 while maintaining a gauge pressure in the cavity 112. In an example, the needle of a syringe can be inserted into or through the septum, such as to place a therapeutic fluid in contact with the eye while maintaining a gauge pressure in the cavity 112.

The enclosure 110 can include a temperature control device, such as to Change the temperature of the therapeutic fluid in the enclosure 110 from a first temperature to a second temperature. The enclosure temperature control device can increase fluid temperature by heating the therapeutic fluid in the cavity 112, such as to change the vasodilation properties of the eye or the therapeutic fluid, such as to increase vasodilation in the eye. The therapeutic fluid can be heated in the enclosure 110, such as by conduction using an electrical resistance heating element in contact with one or more surfaces of the enclosure 110. In an example, the electrical resistance heating element can be in contact with the generally concave inner surface of the enclosure 110, the generally convex outer surface of the enclosure 110, or embedded within the enclosure 110, such as between the inner and outer surfaces of the enclosure. The electrical resistance heating element can be electrically connected to a power source, such as the processor module 140 or a wall outlet.

In an example, the apparatus 100 can include a first enclosure 110A and a second enclosure 110B, such as to form a pair of goggles. Enclosures 110A and 110B can be joined together by a bridge 119, such as an adjustable bridge that can be fit to a specific patient. The bridge 119 can include a pressure tube 1170 connected to enclosures 110A and 110B, such as the cavity 112A formed by enclosure 110A can be in fluidic communication with the cavity 112B formed by enclosure 110B. In an example, the fluid pressure in cavity 112A can be the same or about the same as the fluid pressure in cavity 112B. In an example, the enclosure 110 can be sized and shaped to surround two patient eyes where the cavity 112 can be in communication with both eyes simultaneously, such as in a manner similar to a diving facemask.

The fluid regulator 120 can regulate the flow of fluid between two reservoirs, such as the fluid flow between a first reservoir at a first pressure and a second reservoir at a second pressure different from the first pressure. The fluid regulator 120 can include a valve, such as to regulate flow rates between the first and second reservoirs. The valve can include a passive valve, such as a check valve that closes as pressure exceeds a critical value. In an example, a fluid regulator 120A with a check valve can be located between the enclosure 110A and a fluid source 170, such as if the pressure of the fluid source 170 exceeds a critical value, such as a pressure that can cause damage to a patient eye, the check valve can close to isolate pressure of the fluid source 170 from the patient eye, such as to protect the patient eye from excessive force. The valve can include an active valve, such as a servo (or electrically-modulated) valve. In an example, the servo valve can receive a control signal, such as from the control circuit, to modulate the position of the servo spool with respect to the valve body, such as to regulate fluid flow through the valve.

The fluid regulator 120 can attach to a fluid source 170, such as to regulate the flow of fluid from the fluid source 170 to the cavity 112. The fluid source 170 can include a storage container, such as a storage container of pressurized therapeutic fluid. A storage container can include a disposable or recyclable receptacle, such as a single-use cartridge, or a refillable receptacle, such as a multi-use container or cartridge. The fluid source 170 can include a generator device, such as a device that concentrates or distills a therapeutic fluid from another fluid. In an example, a generator device can include a concentrator, such as an oxygen concentrator or a carbon dioxide concentrator. In an example, a generator device can include an atomizer, such as an ultrasonic humidifier or an aerosolizer, to transform a therapeutic liquid, such as an miscible solution or colloidal suspension, into a therapeutic gas, such as a therapeutic mist or fog.

The fluid regulator 120 can be connected to the apparatus 100, such as to place the output of the fluid regulator 120 in communication with the cavity 112. In an example, the fluid regulator 120A can be connected to the enclosure 110A, such as with the pressure tube 117D in direct communication with the enclosure 110A. In an example, the fluid regulator 120B can be connected to the pressure tube 117B in communication with the enclosure 110B by a tube connector 118, such as a Y-connector. In an example, the fluid regulator 120C can be connected to the processor module 140, such as to be in communication with the enclosure 110A by the pressure tube 117A connected to the processor module 140.

An indication of the eye can include a characteristic of the eye, such as a physical characteristic, that can vary over time, such as due to physiological changes in the eye or in response to a therapy applied to the eye. A physical characteristic of the eye can include at least one of an intraocular pressure (or IOP), a translaminar pressure difference (or TPD), a cup-to-disc ratio, a caliber of a blood vessel in the eye, such as a change in the caliber of the blood vessel, or displacement of the lamina cribrosa, such as a change in the displacement of the lamina cribrosa.

An indication of the environment, such as the therapeutic environment in the cavity 112, can include a characteristic of the therapeutic fluid. A characteristic of the therapeutic fluid can include at least one of therapeutic fluid flow, such as in the cavity 112, humidity, pressure, temperature, gas, such as gas composition or partial pressure fraction, or biomarkers, such as bodily substances released from the eye into the cavity 112.

The sensor 130 can sense an indication, such as an indication of the eye and an indication of the therapeutic environment. Sensing an indication of the eye, such as a change in an indication of an eye, can quantify the progression of an eye condition and the effectiveness of an applied treatment. In an example, a characteristic of the eye, such as the cup-to-disc ratio, can change due to an eye condition, such as a change from a first cup-to-disc ratio at a first IOP to a second cup-to-disc ratio at a second IOP greater than the first IOP can suggest the presence of glaucoma. Applied therapies to treat the eye condition can also change the indication of the eye, such as a glaucoma therapy applied to the eye can change the second cup-to-disc ratio to the first cup-to-disc ratio, such as by lowering IOP in the eye.

A physical characteristic of the eye can be sensed with the sensor 130. The sensor 130 can include a human eye, such as in combination with a slit lamp, such as with or without magnification, an imaging device, such as a digital camera, an optical coherence tomography (OCT) imaging system, or a blood vessel characteristic detector, such as the detectors and methods described in the U.S. Patent Application No. 62/210,751 by Berdahl, filed on Aug. 27, 2015 which is incorporated herein by reference in its entirety.

The sensor 130 can be located outside the eye, such as in proximity to but apart from the apparatus 100. In an example, the sensor 130, such as the OCT imaging system, can be used to detect a first position of the lamina cribrosa subject to a first condition of the eye, such as a first intraocular pressure (IOP), and a second position of the lamina cribrosa subject to a second condition of the eye, such as a second IOP. In an example, the sensor 130, such as a blood vessel characteristic detector, can be used to detect a characteristic of a blood vessel, such as a first caliber of an episcleral blood vessel subject to a first IOP, and a second caliber of the episcleral blood vessel subject to a second IOP. The OCT and blood vessel characteristic detector can be located in an office, such as the office of a medical professional, for use during periodic eye exams, such as to document the progression of a chronic eye condition and suggest treatment regimens to address the eye condition.

The sensor 130 can be located inside the eye, such as within the intraocular space of the eye. The sensor 130 can include a device that can detect pressure, such as the IOP of the eye implanted with the sensor 130. The sensor 130 can be located within the intraocular space of the eye to detect a first IOP of the eye subject to a first condition of the eye, and a second IOP of the eye subject to a second condition of the eye, such as to determine the effect of a gaseous therapy treatment delivered by the apparatus 100 to the eye. In an example, the sensor 130 can include a sensor system, such as the detectors and methods described in the U.S. patent application Ser. No. 13/818,497 by Ostermeier, filed on Feb. 22, 2013 which is incorporated herein by reference in its entirety and the WIT eye pressure measurement system from Implandata Ophthalmic Products GmbH (Hannover, Germany) described in the publication "An Implantable Intraocular Pressure Transducer Initial Safety Outcomes", by Melki, et al., JAMA Ophthalmology, published online Jun. 26, 2014, and incorporated herein by reference in its entirety. The sensor 130 located in the eye can provide continuous sensing of an indication of the eye, such as IOP, for use during treatment of the eye condition, such as with the apparatus 100, to vary the therapeutic environment, such as the composition and pressure of the therapeutic fluid, with a controller, such as a closed loop controller, to improve patient treatment.

The sensor 130 can sense an indication of the therapeutic environment in the cavity 112, such as a characteristic of the therapeutic fluid in contact with the eye, such as at least one of therapeutic fluid flow, humidity, pressure, temperature, or medicinal fluid concentration. The sensor 130 can be located in proximity to the apparatus 100, such as in communication with the cavity 112, and can provide continuous sensing of the therapeutic fluid, such as for use as a feedback parameter in a closed-loop control system. The indication of the therapeutic environment can be received by the processing module 140, such as by a PID controller, to control the composition and pressure of the therapeutic fluid in the cavity 112, such as adhere to a therapy regimen prescribed by a medical professional to treat an eye condition.

The sensor 130 can include a flow sensor, such as a device to sense an indication of the flow of the therapeutic fluid introduced into the cavity 112. The sensor 130 can include a humidity sensor, such as a device to sense an indication of the relative humidity of the therapeutic fluid in the cavity 112. The sensor 130 can include a pressure sensor, such as a device to sense an indication of the pressure of the therapeutic fluid in the cavity 112. The sensor 130 can include a thermometer, such as a device to sense an indication of the temperature of the therapeutic fluid in the cavity 112.

The sensor 130 can include a gas sensor, such as a device to sense an indication of a gaseous substance in the therapeutic fluid, such as a percent concentration of the gaseous substance in the therapeutic fluid. In an example, the gaseous substance can include a medicinal gas, such as a constituent of the therapeutic fluid delivered to the cavity 112. In an example, the gaseous substance can include a biomarker, such as a biomarker emitted by the eye.

A biomarker can include ketones, such as can be detected with a volatile gas sensor including a quartz crystal nanobalance (QCN) sensor, glucose, such as can be detected with an optical glucose sensor including an OCT imaging system, oxygen levels, such as can be detected with a non-invasive optical oxygen sensor, dissolved salts, such as can be detected with a salinity sensor, and vascular endothelial growth factor (or VEGF), such as can be detected with an aptamer-based sensor including the sensor and methods described in the publication "Flexible FET-Type VEGF Aptasensor Based on Nitrogen-Doped Graphene Converted from Conducting Polymer", by Kwon, et at., ACS Nano, Vol. 6, #2, pages 1486-1493, published February 2012, and incorporated herein by reference in its entirety. Biomarkers can suggest a physiological state of the eye, such as a state of stability or a state of distress, such as where medical intervention can be required.

The sensor 130 can include a pulse oximeter device, such as a device to sense an indication of systemic oxygen levels. In an example, the indication of systemic oxygen levels can be received by the processing module 140 and oxygen concentration in the therapeutic fluid adjusted, such as increased, to maintain oxygenation of the eye even in the presence of low systemic oxygen levels.

The processor module 140 can provide a communication interface, such as to allow a user to operate the apparatus 100. The communication interface can include an operations unit, such as for a user to manage basic functionality of the apparatus 100, such as cycling the power of the apparatus 100. The communication interface can include a data acquisition unit to record an indication, such as an indication of the therapeutic fluid in the cavity 112 or an indication of the eye, over a period of time. In an example, the indication can be recorded for a relatively short period of time, such as for health screening purposes, or for a relatively long period of time, such as for monitoring the effect of a prescribed treatment on the eye condition treated.

The processor module 140 can control the operation of the apparatus 100, such as the apparatus can operate in a feedback or closed-loop control mode. The processor module 140 can be in communication, such as electrical communication, with at least one of the regulator 120, the sensor 130, or the pump 150, such as to coordinate operation of the components. The processor module 140 can receive a signal, such as a signal proportional to an indication of the eye or the environment, from the sensor 130 and process the signal, such as to compare a first signal to a second signal, such as to find a difference between the first and second signals. The processor module 140 can include a control circuit, such as to implement a control algorithm including a feedback control algorithm. In an example, the control circuit can include a controller, such as a proportional-integral-derivative (or PID) controller. In operation, the control circuit can receive a signal from the sensor 130, such as an electrical signal proportional to changes in the sensed indication, process the signal, such as with a PID controller to minimize a steady state error between the sensor signal and a set point, such as a specified user-defined set point, and generate a control signal, such as to adjust the operational state of at least one of the regulator 120, a manifold vent 144, or the pump 150.

The processor module 140 can include a power source, such as to supply electrical energy to the apparatus 100. In an example, the power source can include a battery, such as a lithium ion battery, and a transformer, such as to receive power from a wall outlet for use in the apparatus 100 at a specified voltage and current. The processor module 140 can include a heating element, such as a heating element in communication with the therapeutic fluid including a heating element located on a surface of the mixing chamber 146, to increase the temperature of the therapeutic fluid.

FIG. 1B shows an example of a manifold 149, such as a manifold 149 that can be in communication with the processing module 140, such as in electrical communication, and the pump 150, such as in fluidic communication. The manifold can include a mixing chamber 146, such as to fluidically connect the fluid regulator 120C and the pump outlet 155 with the pressure tube 117, such as the pressure tube 117A. In operation, volumetric fluid flow from the pump outlet 155 can combine with a medicinal fluid, such as from the fluid source 170 via the fluid regulator 120C, to form a therapeutic fluid in the mixing chamber 146. The therapeutic fluid can exit the mixing chamber 146 through the pressure tube 117A, such as for introduction into the cavity 112A.

The manifold 149 can include an inlet chamber 148, such as to fluidically connect the pump inlet 156 with the pressure tube 117, such as pressure tube 117B in fluidic communication with the cavity 112B, and the manifold vent 144, such as in communication with the ambient environment.

The manifold 149 can include a vent 144 in fluid communication with the cavity 112, such as to adjust the gauge pressure within the enclosure 110. The vent 144 can communicate with the processor module 140 to open and close the vent 144, such as to maintain a desired gauge pressure within the cavity 112. In an example, as a gauge pressure sensed by a sensor 130 in the cavity 112 exceeds a predetermined threshold value, the vent 144 can receive a control signal from the control circuit, such as to modulate the vent 144 to maintain a desired gauge pressure within the cavity 112.

In operation, the pump 150 can create a region of low pressure at the pump inlet 156, such as to draw therapeutic fluid from the pressure tube 117B and ambient fluid, such as air at standard temperature and pressure, from the manifold vent 144. The composition of the therapeutic fluid can be adjusted by the amount of ambient air drawn from the manifold vent 144.

The pump 150 can generate a volumetric fluid flow, such as by using fluid from the apparatus 100, such as the cavity 112, or from an external source. The pump 150 can include a passage 157, such as between the pump inlet 156 and the pump outlet 155, and a fan 153 located at least partially in the passage 157, such as a centrifugal fan capable of generating a volumetric fluid flow. The pump 150 can include a filter 158, such as a particulate filter to remove dust and a desiccant filter to remove water vapor (i.e., humidity) from fluid flow in communication with the passage 157, and a pump vent 159 in communication with the passage 157 and the surrounding environment, such as to allow for the introduction of ambient air into the apparatus 100. The pump 150 can include a power source 152, such as a battery, and be in communication with the enclosure 120, the sensor 130, and the processor module 140.

In operation, rotation of the fan 153 in the passage 157 can draw fluid from an inlet, such as from the pump inlet 156 including the vent 144 and the pump vent 159, to generate a volumetric fluid flow at an outlet, such as the pump outlet 155. The filter 158 can be located in the passage 157, such as between the pump inlet 156 and the fan 153 or the fan 153 and the pump outlet 155. Exposure of the filter 158 to the fluid flow can be regulated, such as the volume of fluid flow passing through the filter can be controlled, such as to adjust a parameter of the therapeutic fluid. In an example, the humidity in the therapeutic fluid can be adjusted, such as decreased, by exposing at least a portion of the therapeutic fluid to the filter 158, such as a desiccant filter. Exposure of the filter 158 to the therapeutic fluid can be regulated with a slide valve, such as a slide valve attached to an actuator and in electrical communication with the control circuit of the processing module 140. In an example, water vapor can be entrained in the desiccant filter, such as until the desiccant filter can be saturated, and thereafter eliminated from the apparatus 100, such as by replacing the saturated desiccant filter 158 or by heating the desiccant filter 158, such as to cause the water vapor to evaporate from the desiccant filter 158.

The pump 150 can apply and maintain a gauge pressure in the cavity 112 and distribute fluid, such as therapeutic fluid, in the cavity 112. The applied gauge pressures can vary in a range from about −40 mmHg to about 40 mmHg, such as in a range from about −20 mmHg to about 20 mmHg, in a range of about −10 mmHg to about 10 mmHg, in a range of about −5 mmHg to about 5 mmHg, in a range of about −1 mmHg to about 1 mmHg, or in a range of about −0.5 mmHg to about 0.5 mmHg. In an example, the pump 150 can apply a gauge pressure to the cavity 112 at a level of at least one of −40 mmHg, −35 mmHg, −30 mmHg, −25 mmHg, −20 mmHg, −15 mmHg, −10 mmHg, −5 mmHg, −4 mmHg, −3 mmHg, −2 mmHg, −1 mmHg, −0.9 mmHg, −0.8 mmHg, −0.7 mmHg, −0.6 mmHg, −0.5 mmHg −0.4 mmHg, −0.3 mmHg, −0.2 mmHg, 0.1 mmHg, −0.09 mmHg, −0.08 mmHg, −0.07 mmHg, −0.06 mmHg, −0.05 mmHg, −0.04 mmHg, −0.03 mmHg, −0.02 mmHg, −0.01 mmHg, 0.01 mmHg, 0.02 mmHg, 0.03 mmHg, 0.04 mmHg, 0.05 mmHg, 0.06 mmHg, 0.07 mmHg, 0.08 mmHg, 0.09 mmHg, 0.1 mmHg, 0.2 mmHg, 0.3 mmHg, 0.4 mmHg, 0.5 mmHg, 0.6 mmHg, 0.7 mmHg, 0.8 mmHg, 0.9 mmHg, 1 mmHg, 2 mmHg, 3 mmHg, 4 mmHg, 5 mmHg, 10 mmHg, 15 mmHg, 20 mmHg, 25 mmHg, 30 mmHg, 35 mmHg, or 40 mmHg.

The appropriate duration to apply therapeutic fluids, such as a therapeutic fluid applied with or without a gauge pressure, can vary depending on the eye condition treated. A therapeutic regimen for an acute eye condition can require application of a therapeutic fluid, such as with or without gauge pressure, for relatively short periods of time, such as for periods of time measured in minutes, hours, days, or weeks. In an example, a therapeutic regimen to treat an acute eye condition can include application of a therapeutic fluid with the apparatus 100 for at least one of 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours. 18 hours, 19 hours, 20 hours, 21 hours, 22 hours, 23 hours, and 24 hours, 1 day, 2 days, 3 days, 4 days, 5 days, 6 days, and 7 days, 1 week, 2 weeks, 3 weeks, or 4 weeks.

Therapeutic regimens for chronic eye conditions, such as glaucoma, can require application of a therapeutic fluid, such as with or without gauge pressure, for relatively long periods of time, such as for periods of time measured in days, weeks, months or years. In an example, a therapeutic regimen to treat a chronic eye condition can include application of a therapeutic fluid with the apparatus 100 for at least one of 1 day, 2 days, 3 days, 4 days, 5 days, 6 days, and 7 days, 1 week, 2 weeks, 3 weeks, and 4 weeks, 1 month, 2 months, 3 months, 4 months, 5 months, 6 months, 7 months, 8 months, 9 months, 10 months, 11 months, and 12 months, 1 year, 2 years, 3 years, 4 years, 5 years, 6 years, 7 years, 8 years, 9 years, or 10 years. In an example, a therapeutic regimen to treat a chronic eye condition, such as glaucoma and optic disc edema, can include the application of a therapeutic fluid, such as with or without gauge pressure, delivered to the eye with the apparatus 100 for the lifetime of the patient.

The pump 150 can modulate the therapeutic fluid, such as with or without gauge pressure, applied to the cavity 112, such as periodically and aperiodically. A periodic gauge pressure can include a gauge pressure that can vary in magnitude at regular intervals, such as with sinusoidal signals, periodic non-sinusoidal signals, and repeating processes. In an example, the gauge pressure applied to the enclosure 110 can vary in a substantially sinusoidal fashion with a period of approximately 24-hours, such as to compensate for the natural diurnal cycle of IOP in the eye of the patient. A periodic gauge pressure can include gauge pressures that vary in frequency, such as the time between repeating intervals in the periodic signal. In an example, the gauge pressure applied to the enclosure can vary in frequency, such as when the gauge pressure applied to the cavity 112 can vary as a function of cardiac activity, such as heart rate and blood pressure, the cardiac activity measured by a detection device, such as a blood pressure monitoring device in communication with the processing module 140.

An aperiodic gauge pressure can include gauge pressures that vary in magnitude at irregular intervals, such as non-periodic signals and non-repeating processes. The gauge pressure applied to the enclosure can vary in an aperiodic fashion that is dependent upon an indication of a body parameter, such as the position of a patient with respect to a coordinate system. In an example, an indication of a body position can include a change in body position, such as the change in body position of a patient transitioning from a first body position, such as a standing position, to a second body position, such as a sitting or prone position. The gauge pressure applied to the enclosure 110 can vary in an aperiodic fashion that is dependent upon the summation of one or more periodic and aperiodic signals. In an example, the gauge pressure applied to the enclosure 110 can include a periodic component, such as the gauge pressure due to cardiac activity, and an aperiodic components, such as the gauge pressure due to the body position of a patient.

Figure 5:
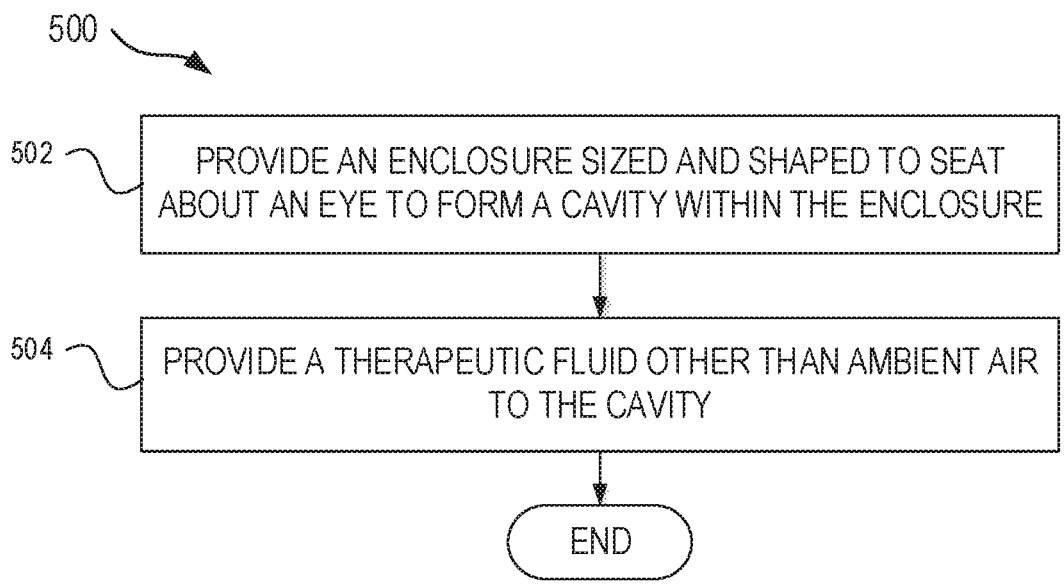
FIG. 5 shows an example method for introducing a gaseous fluid other than ambient air into one or more cavities within the enclosure.

FIG. 5 shows an example method 500 for introducing a fluid, such as a gaseous therapeutic fluid other than ambient air, into a cavity 112. At 502, an enclosure 110 can be provided, such as an enclosure 110 sized and shaped to be seated about an eye, such as to form a cavity 112 within the enclosure 110 over the eye. The enclosure 110 can include a gasket 114 that can be seated between the enclosure 110 and the skin of the patient to form a seal between the enclosure 110 and the skin of the patient. The gasket 114 can be selected to form a resistance flow path between the therapeutic environment within the cavity 112 and the surrounding environment, such as the resistance can be dependent upon the gasket used. In an example, the gasket 114 can form a 'loose' seal between the enclosure 110 and the patient, such as to allow some leakage of fluid from the cavity 112 through the resistance flow path to the surrounding environment, such as to maintain a slight gauge pressure in the cavity 112. In an example, the gasket 114 can form a 'tight' seal between the enclosure 110 and the patient, such as to largely prevent leakage of fluid from the cavity 112 through the resistance flow path to the surrounding environment, such as to maintain a substantial gauge pressure in the cavity 112. In an example, the gasket 114 can form a hermetic seal that can prevent leakage of fluid from the cavity 112 to the surrounding environment.

At 504, a fluid, such as therapeutic fluid other than ambient air, can be provided to the cavity 112. The therapeutic fluid can include medicinal fluids, such as pure gases including nitric oxide and carbon dioxide, and combinations of medicinal gases. In an example, a combination of medicinal gases can include a combination of nitric oxide and carbon dioxide, such as to affect vasodilation of an eye by increasing aqueous humor outflow to lower IOP. The percentage of nitric oxide and carbon dioxide can be specified to achieve a specific endpoint, such as to maximize vasodilation of an eye based on the physiology of a specific patient. The percentage of nitric oxide can include specified percentages of nitric oxide, such as 1%, 2%, 3%, 5%, 10%, 15%, 70%, 25%, 30%, 35%, 40%, 45%, 50%, 55%, 60%, 65%, 70%, 75%, 80%, 85%, 90%, 95%, 96%, 97%, 98% 99%, or other percentages.

In an example, a combination of gases can include a combination of nitric oxide and oxygen, such as to provide increased oxygen concentration to tissues, such as eye tissues, while increasing vasodilation of an eye, such as by increasing aqueous humor outflow to lower IOP. The percentage of nitric oxide and oxygen can be specified to achieve a specific endpoint, such as to maximize eye tissue oxygen saturation based on the physiology of a specific patient.

The gaseous therapeutic fluid can include water vapor, such as humidity. The humidity of the therapeutic fluid can include a specified humidity, such as a specified percentage humidity (e.g., relative humidity), such as 1%, 2%, 3%, 5%, 10%, 15%, 20%, 25%, 30%, 35%, 40%, 45%, 50%, 55%, 60%, 65%, 70%, 75%, 80%, 85%, 90%, 95%, 96%, 97%, 98% 99%, or other percentages.

The therapeutic fluid provided to the cavity 112 can be in contact with the eye, such as the anterior surface of the eye including the corneal, scleral, and conjunctival surfaces of the eye, so that the therapeutic fluids can pass into the eye, such as through absorption of the therapeutic fluid through the surfaces of the eye. The composition of the therapeutic fluid can be controlled, such as with a fluid regulator 120. The fluid regulator 120 can include a passive valve, such as a check valve that closes as pressure exceeds a critical value, such as a pressure that can damage a patient eye. In an example, where the pressure of the fluid source 170 can be less than the critical value, fluid can flow between the cavity 112 and the fluid source 170. In an example, where the pressure of the fluid source 170 can be equal to or greater than the critical value, the check valve can close, such as to prevent damage to the patient eye. In an example, the critical value can be adjusted, such as the check valve can be adjusted from a first critical value to a second critical value, such as a second critical value different from the first critical value.

Figure 6:
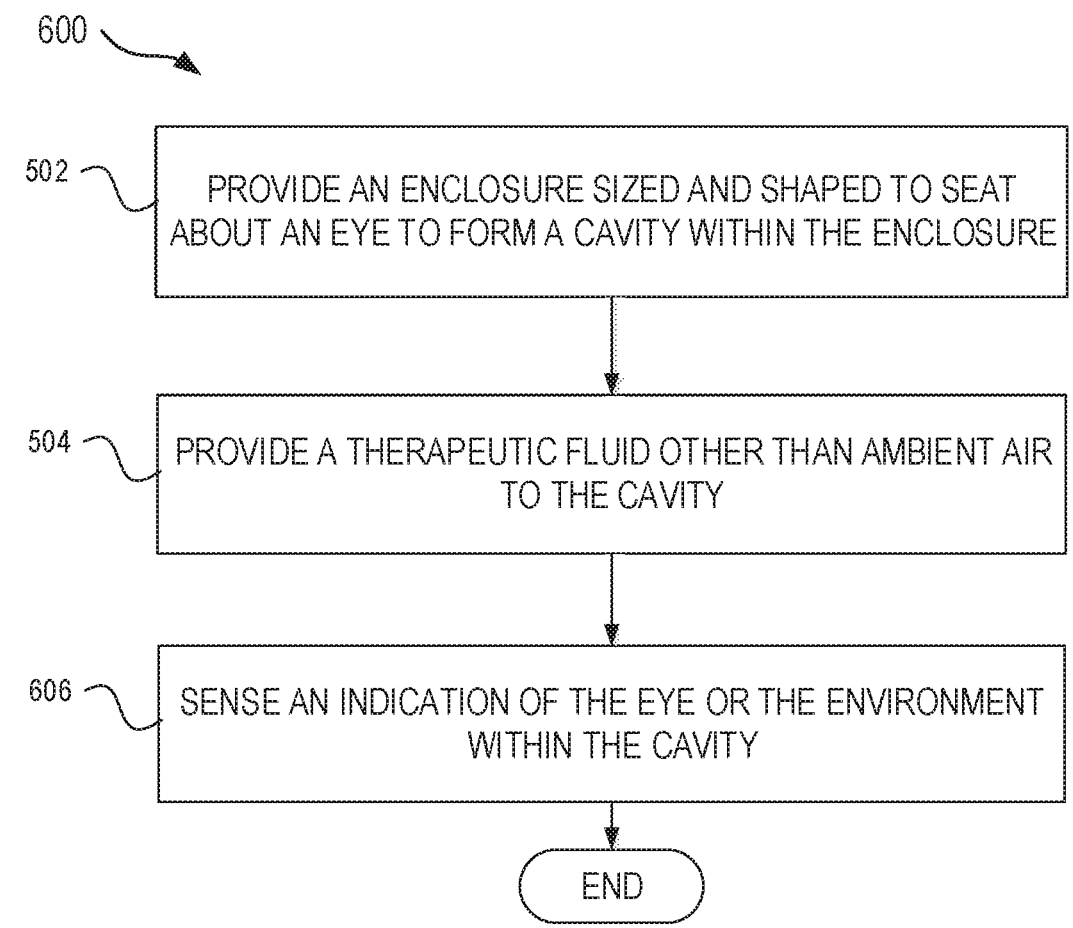
FIG. 6 shows an example method of sensing an indication with the apparatus.

FIG. 6 shows an example method 600 of sensing an indication with the apparatus 100. At 606, an indication of the eye or an indication of the environment in the cavity 112 can be sensed, such as with a sensor 130. Sensing an indication of the eye can include sensing a physical characteristic of the eye, such as a change in a physical characteristic. The physical characteristic can be sensed periodically, such as to track progression of an eye condition as a part of an eye exam, or continuously, such as a feedback parameter in a closed-loop control system configured to adjust the composition of the therapeutic fluid in the cavity 112.

Sensing an indication of the environment can include sensing a characteristic of the therapeutic fluid in the cavity 112, such as the level of the characteristic or a change in the level of the characteristic. In an example, the sensor 130 can sense a level of fluid concentration or a change in fluid concentration, such as the concentration of a medicinal fluid in the therapeutic fluid. The therapeutic fluid characteristic can be sensed periodically, such as on a daily or hourly schedule, or continuously.

Figure 7:
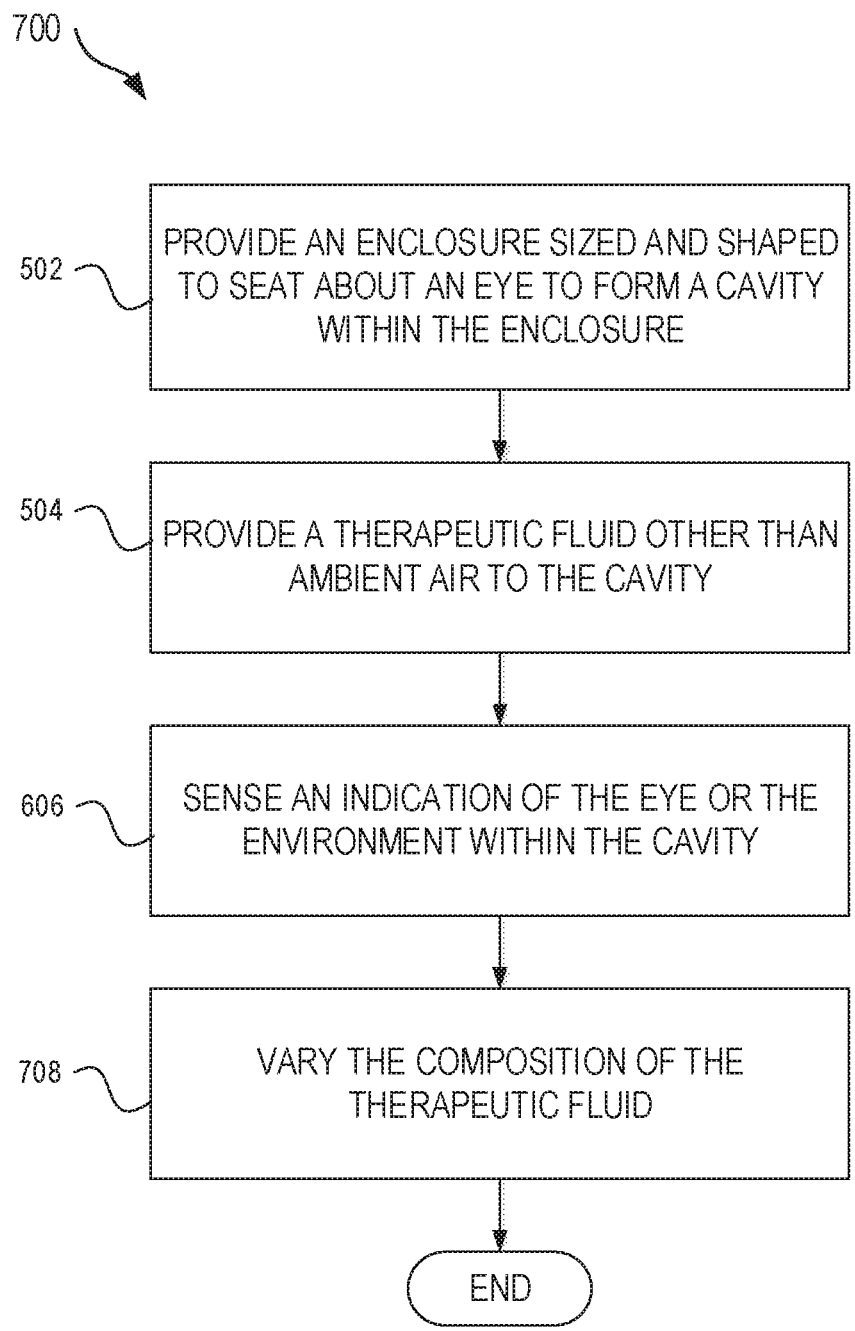
FIG. 7 shows an example method for varying the composition of the gaseous fluid within the cavity.

FIG. 7 shows an example method 700 for adjusting a therapeutic fluid within the cavity 112. At 708, the therapeutic fluid, such as the composition of the therapeutic fluid, can be varied. Varying the therapeutic fluid can include changing the composition of the therapeutic fluid, such as by varying the concentration of a constituent fluid, such as a medicinal gas, within the therapeutic fluid.

Varying the composition of the therapeutic fluid can include manually adjusting the concentration of a constituent fluid, such as by adjusting a valve on the fluid regulator 120. In an example, upon recognizing worsening symptoms of an eye condition an eye patient can vary the composition of the therapeutic fluid provided to the cavity 112, such as by increasing the flow of medicinal fluid to the cavity 112, such as by manually opening the check valve of a fluid regulator 120, until the symptoms of the eye condition dissipate.

Varying the composition of the therapeutic fluid can include operating the apparatus 100 with an open-loop control algorithm, such as with a controller varying therapeutic composition at predetermined times. Eye pressure of a patient can vary throughout the day, such as IOP can be elevated during the active hours of the day and lowered during the inactive hours. In an example, the apparatus 100 can manage IOP therapy, such as with a control circuit operating an open-loop algorithm where the control circuit can be connected to a servo valve, the control circuit programmed to initiate a preset pattern based on time of the day. For example, the control circuit can adjust the servo valve of a fluid regulator 120 to increase oxygen concentration in the therapeutic fluid during hours when the patient can be active and decrease oxygen concentration in the therapeutic fluid during hours when the patient can be inactive.

Varying the composition of the therapeutic fluid can include operating the apparatus 100 with a closed-loop control algorithm, such as with a controller varying therapeutic composition in response to receiving a first feedback parameter, such as an indication of the eye. In an example, a sensor 130, such as a digital camera, can sense a change in an indication of the eye, such as a change in the cup-to-disc ratio of the eye. The digital camera can sense a change in cup-to-disc ratio, such as by comparison of a first image captured at a first time instance and a second image captured at a second time instance and identifying the difference between the first and second images, such as with the processing module 140. A controller, such as a PID controller, can receive a signal from the sensor 130 proportional to the indication of the eye and issue a control signal, such as to the fluid regulator 120, to vary the composition of medicinal fluid, such as to counteract the change in the cup-to-disc ratio sensed by the sensor 130.

Varying the composition of the therapeutic fluid can include receiving a second feedback parameter, such as an indication of the environment in the cavity 112. In an example, a sensor 130, such as a gas sensor, can sense an indication of the therapeutic fluid, such as the concentration of a medicinal fluid. A controller can receive a signal from the sensor 130 proportional to the indication of the therapeutic fluid and compare the received signal to a set point value. Where the concentration of the medicinal fluid falls below the set point value, the controller can issue a control signal to the fluid regulator 120 to vary the fluid flow of a medicinal fluid from the fluid source 170, such as to increase medicinal fluid concentration in the therapeutic fluid and minimize the difference in the received signal and the set point value. Where the concentration of the medicinal fluid exceeds the set point value, the controller can issue a control signal to the pump 150, such as the fan 153, to increase volumetric fluid flow, such as to decrease or dilute medicinal fluid concentration in the therapeutic fluid and minimize the difference in the received signal and the set point value.

Figure 8:
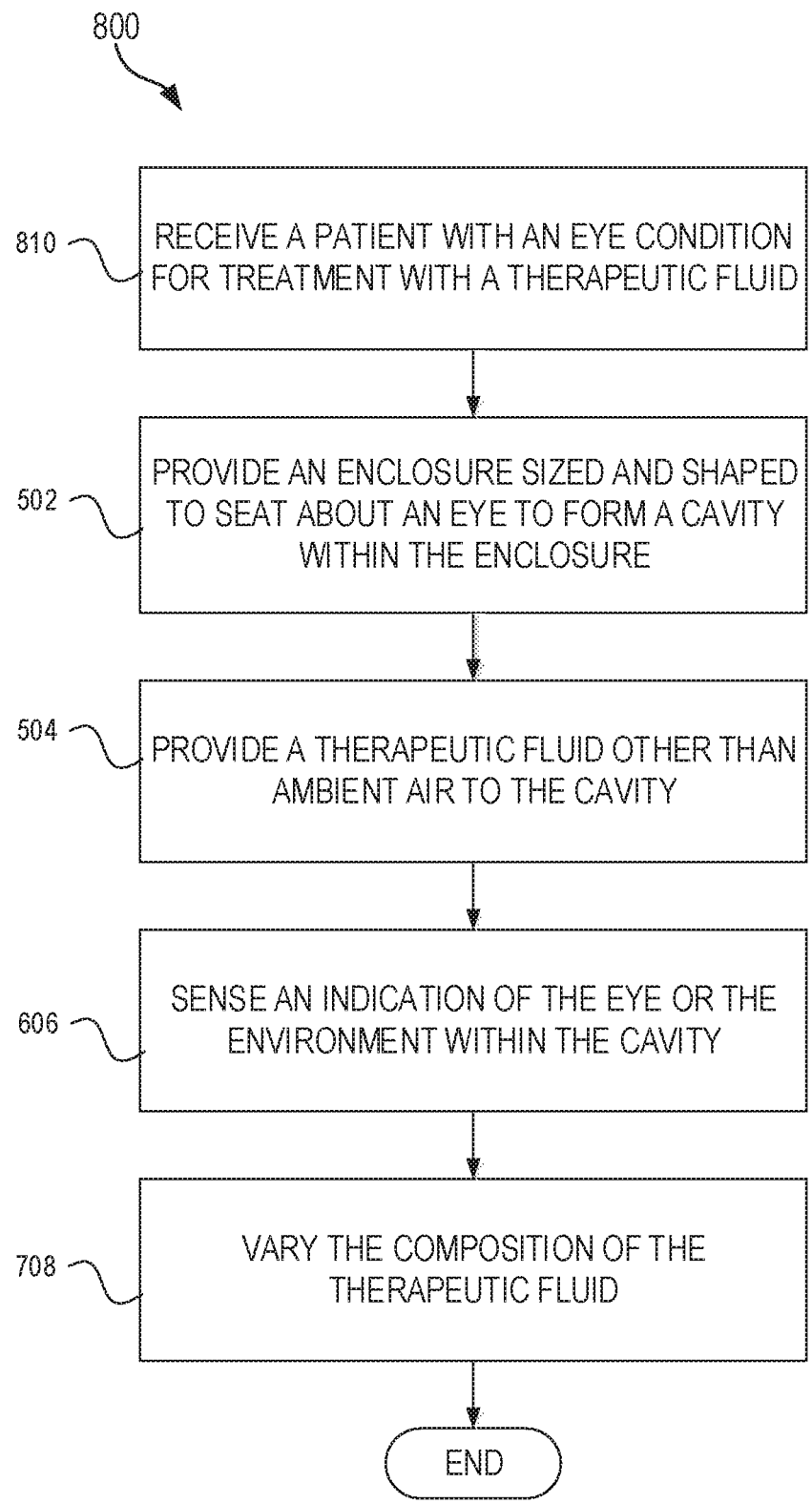
FIG. 8 shows an example method for receiving a patient.

FIG. 8 shows an example method 800 for receiving a patient. At 810, receiving a patient can include receiving a patient with an eye condition for treatment with the therapeutic fluid.

Eye conditions including glaucoma, dry eye, diabetic retinopathy, cataract, venous and arterial occlusive diseases, macular degeneration, diseases of the cornea, endothelium, and epithelium, diseases of the retinal vasculature, diseases of the retinal pigmented epithelium, corneal infections, or other infections of the eye can be treated with a therapeutic fluid, the therapeutic fluid including a medicinal fluid, such as at least one of carbon dioxide, oxygen, or nitric oxide. The specified non-ambient concentration of medicinal fluid in the therapeutic fluid can include a percentage concentration, such as 1%, 2%, 3%, 5%, 10%, 15%, 20%, 25%, 30%, 35%, 40%, 45%, 50%, 55%, 60%, 65%, 70%, 75%, 80%, 85%, 90%, 95%, 96%, 97%, 98% 99%, or other percentages. In an example, the therapeutic fluid can include between 50 percent and 80 percent carbon dioxide ($CO_2$), such as to treat glaucoma. In an example, the therapeutic fluid can include between 50 percent and 95 percent oxygen ($O_2$), such as to treat diabetes or Fuchs' dystrophy. In an example, the therapeutic fluid can include between 10 percent and 90 percent nitric oxide (NO), such as to treat glaucoma.

The example method 800 can be used to treat an eye, such as to potentiate a therapeutic substance in contact with the eye. Potentiation can be described as the interaction between two or more therapeutic agents that results in a pharmacologic response greater than the sum of responses to each agent individually. A first potentiating therapeutic agent can include a therapeutic fluid, such as at least one of riboflavin, decorin, anti-VEGF, antibiotics, antiviral, or antifungal fluids. A second potentiating therapeutic agent can include a source of radiating energy, such as at least one of incoherent light, infrared (IR) light, ultraviolet (UV) light, coherent light, such as realized with a laser, or a medicinal fluid.

In an example, the method 800 can potentiate a first set of therapeutic agents, such as to treat corneal ectasia including keratoconus, pellucid marginal degeneration (PMD), and post-LASIK ectasia, by corneal collagen cross-linking. At 810, a patient suffering from corneal ectasia can be received. At 502, an enclosure sized and shaped to seat about an eye can form a cavity 112 over the eye. At 504, a first potentiating therapeutic agent, such as a gaseous fluid other than ambient air including a fluid with a specified concentration of riboflavin, and a second potentiating therapeutic agent, such as radiation energy including UV-A light, can be introduced into the cavity 112. Gaseous riboflavin can be absorbed into the anterior surface of the eye and exposure to UV-A light, such as exposure through the enclosure 110 irradiating the eye and the riboflavin-rich therapeutic fluid, can potentiate the absorbed riboflavin, such as to form additional bonds between adjacent collagen strands in the stromal layer of the cornea, to improve the strength and elasticity of the cornea. At 606, an indication of the concentration of riboflavin can be sensed in the cavity 112, such as to indicate the amount of riboflavin absorbed by the eye. At 708, the concentration of riboflavin can be varied, such as increased or decreased, such as to a physician-recommended concentration.

In an example, the method 800 can potentiate a second set of therapeutic agents, such as a third therapeutic agent including a specified concentration of decorin and a fourth therapeutic agent including a specified concentration of oxygen, in the same manner as the first set of therapeutic agents.

The example method 800 can be used to treat an eye, such as to inhibit infections of the eye. An aerobic infection involves the growth of bacteria requiring free oxygen whereas an anaerobic infection involves the growth of bacteria in the absence of free oxygen.

In an example, the method of 800 can inhibit the growth of infections of the eye, such as by providing an oxygen-deprived environment to stifle growth of an aerobic infection or an oxygen-rich environment to suppress the growth of an anaerobic infection. At 810, a patient suffering from an eye infection, such as an aerobic or an anaerobic infection, can be received. At 502, an enclosure sized and shaped to seat about an eye can form a cavity 112 over the eye. At 504, a therapeutic fluid other than ambient air, such as a nitrogen-rich environment including a therapeutic fluid composed of more than 78% nitrogen to treat aerobic infections and an oxygen-rich environment including a therapeutic fluid composed of more than 21% oxygen to treat anaerobic infections, can be provided to the cavity 112. At 606, an indication of the environment, such as the concentration of a fluid other than ambient air can be sensed in the cavity 112, such as to assess the potency of the infection treatment. At 708, the concentration of a fluid other than ambient air can be varied, such as increased or decreased, such as to a physician-recommended concentration to treat the eye infection.

The example method 800 can be used to treat an eye, such as minimize post-operative damage during the healing process of the eye. In an example, a hypoxic (or oxygen-deprived) environment can reduce corneal scarring and hazing in recuperation of the eye. The method used to treat an infection, such as an aerobic infection as disclosed above, can be used to minimize eye scarring and hazing.

Figure 9:
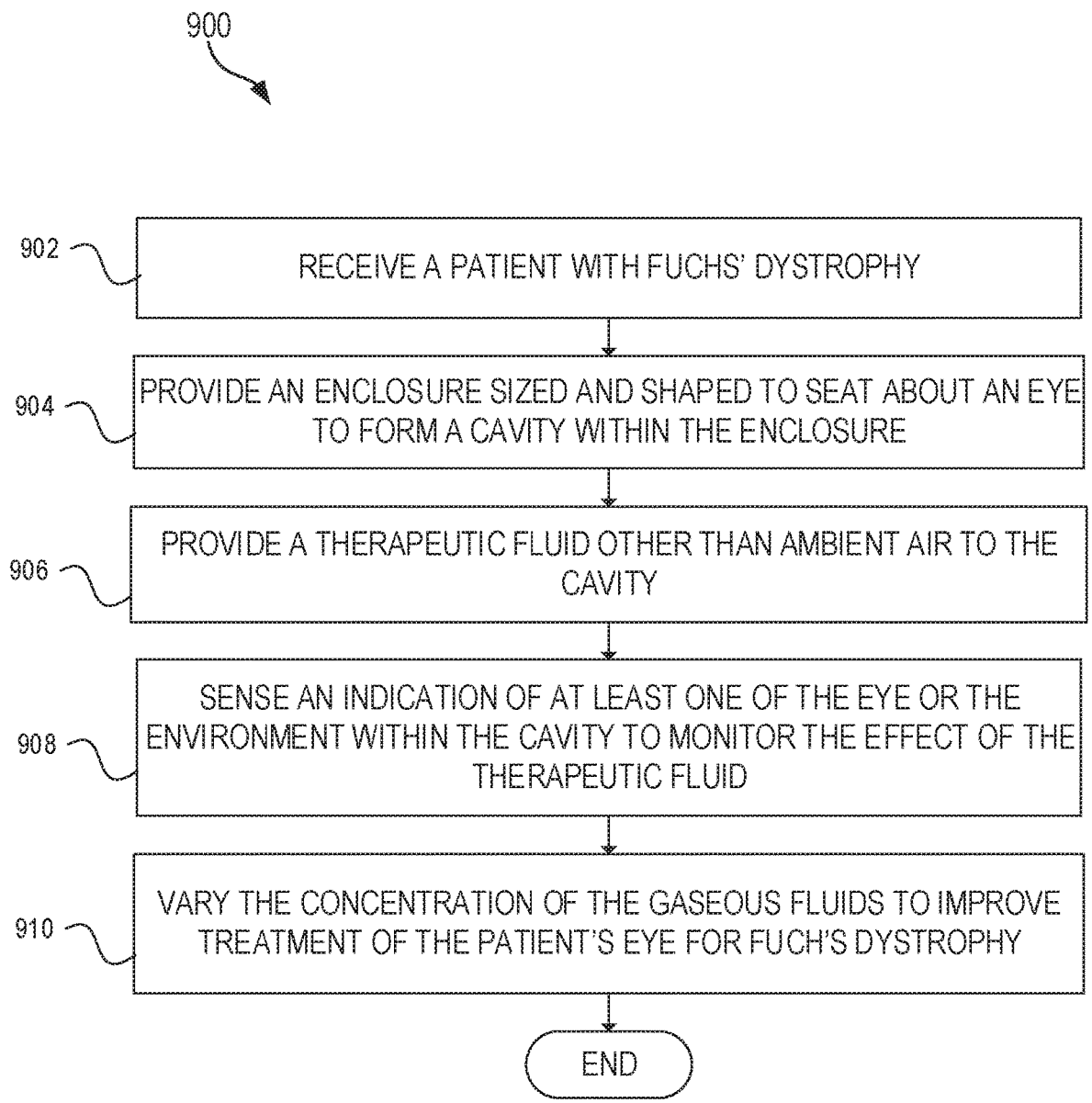
FIG. 9 shows an example of a treatment for Fuchs' dystrophy.

FIG. 9 shows an example method 900 of a treatment for Fuchs' dystrophy. Fuchs' dystrophy can occur when the cornea swells, such as due to endothelial cell dysfunction. Fuchs' dystrophy can be treated by reducing the IOP of the eye and by removing water from the cornea, such as through the application of dehydrating agents including sodium chloride and glycerin to the surface of the eye and evaporation of water from the surface of the eye.

At 902, a patient with an eye condition, such as Fuchs' dystrophy, can be received. At 904, an enclosure 110 can be provided to fit over the eye of the patient, such as to form the cavity 112 between the patient eye and the enclosure 110. At 906, a therapeutic fluid other than ambient air can be provided to the cavity 112, such as to allow the therapeutic fluid to contact the surface of the patient eye. In an example, the therapeutic fluid can include a composition of medicinal fluids, such as a therapeutic fluid with a specified non-ambient concentration of at least one of carbon dioxide ($CO_2$), oxygen ($O_2$), nitric oxide (NO), or water vapor, such as with water vapor in an amount sufficient to realize a desired relative humidity of the composition of gaseous fluids. The specified non-ambient concentration of a constituent of the therapeutic fluid, such as oxygen or relative humidity, can include a percentage concentration, such as 1%, 2%, 3%, 5%, 10%, 15%, 20%, 25%, 30%, 35%, 40%, 45%, 50%, 55%, 60%, 65%, 70%, 75%, 80%, 85%, 90%, 95%, 96%, 97%, 98% 99%, or other percentages. The percentage concentration of the constituent can be selected for a therapeutic purpose. In an example, the gaseous fluid can include between 30 percent and 100 percent oxygen ($O_2$), such as to maintain or improve endothelial cell function in those diagnosed with Fuchs' dystrophy. The treatment of Fuchs' dystrophy, such as the example method 900, can be extended to patients with symptoms similar to Fuchs' dystrophy. In an example, the therapeutic fluid, such as a gaseous fluid including between 30 percent and 100 percent oxygen, can be used to maintain or improve endothelial cell function in people exposed to a high altitude or low oxygen environments, such as astronomers, astronauts, hikers, or others. At 908, at least one of a first sensor 130, such as an OCT imaging system, can sense an indication of the eye, such as a change in the deflection of the lamina cribrosa to estimate IOP, or a second sensor 130, such as a humidity sensor, can sense an indication of the environment, such as the relative humidity within the cavity 112, to monitor the effect of the therapeutic fluid on the patient eye. At 910, the composition of the therapeutic fluid, such as the constituents of the therapeutic fluid and the level of relative humidity, can be varied, such as by adjusting the specified non-ambient concentration of at least one of the constituents of the therapeutic fluid or adjusting the relative humidity, such as to improve the treatment for Fuchs' dystrophy as applied to the patient eye.

Figure 10:
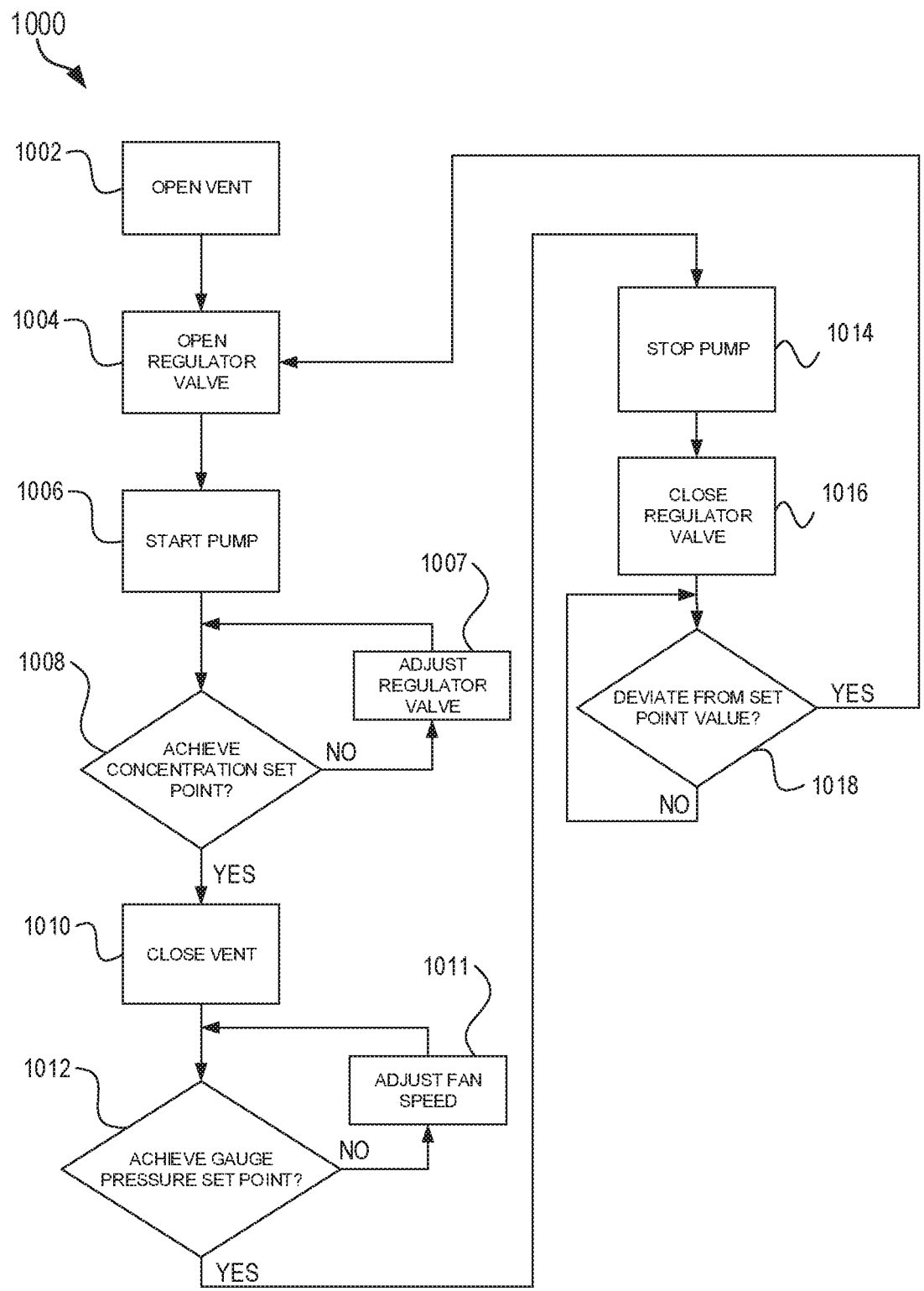
FIG. 10 shows an example method to introduce gaseous fluids into the cavity with a positive gauge pressure.

FIG. 10 shows an example method 1000 to introduce gaseous fluids, such as gaseous fluids other than ambient air, into the cavity 112 with a positive gauge pressure. In an example, a user can interact with the operations unit of the processor module 140, such as to initiate operation of the method 1000.

At 1002, the vent 144 can be opened. Opening the vent 144 can equalize fluid pressure in the apparatus 100, such as in the cavity 112, with the surrounding environment. Equalizing pressure can prepare the cavity 112 to receive a specified gaseous fluid, such as a therapeutic fluid.

At 1004, fluid regulator 120, such as a valve of the fluid regulator 120C, can be opened. Opening the valve of the fluid regulator 120C can allow a fluid, such as a medicinal fluid, to flow out of the fluid source 170 into the processor module 140, such as into a mixing chamber 146 in communication with the pressure tube 117 and the pump outlet 155. In an example, the composition of the therapeutic fluid can be adjusted, such as by changing the outflow rate of the fluid source, such as by opening and closing the valve of the fluid regulator 120C. In an example, the valve can be opened at a predetermined rate, such as in response to a control signal from the processor module 140, to gradually increase the concentration of medicinal fluid released into the mixing chamber 146 over time.

At 1006, the pump 150 can be started to generate volumetric fluid flow, such as to generate a positive gauge pressure at the pump outlet 155. In an example, the pump inlet 156 can be blocked, and the pump outlet 155 can be in direct communication with the mixing chamber 146, such as the volume output can combine with the medicinal fluid flowing through the fluid regulator 120C, such as to create a therapeutic fluid. The composition of the therapeutic fluid can depend on the volume output of the pump 150 and on the volume and concentration of the medicinal fluid flowing through the fluid regulator 120C. In an example, the composition of the therapeutic fluid can be adjusted, such as by changing the volume output of the pump 150. For example, the volume output of the pump 150 can be changed by increasing or decreasing the speed of the pump 150, such as the fan 153 of a centrifugal pump. The therapeutic fluid can flow out of the mixing chamber 146, such as through the pressure tube 117 into the cavity 112.

At 1008, a sensor 130, such as a gas sensor located in the cavity 112, can sense the therapeutic fluid flowing into the cavity 112, such as to sense an indication of the concentration of medicinal fluid in the therapeutic fluid. The processor module 140 can receive a signal from the sensor 130, such as an electrical signal proportional to the indication of the concentration of medicinal fluid in the therapeutic fluid. The received sensor signal can be compared to a predetermined set point value, such as a physician-recommended concentration of medicinal fluid for the treatment of an eye condition, with the control circuit. If the received sensor signal is less than the predetermined concentration set point value, the valve of the fluid regulator 120C can be further opened at 1007, such as to increase the concentration of medicinal fluid in the mixing chamber 146, and the therapeutic fluid can be re-sensed at 1008. The valve of the fluid regulator 120C can continue to open until the received sensor signal, such as sensed in the cavity 112, reaches the predetermined concentration set point value.

At 1010, the vent 144 can be closed. After the received sensor signal meets the predetermined set point value, the therapeutic fluid can be considered adequately mixed in the apparatus 100 at the pressure of the surrounding environment, such as the local ambient pressure. The vent 144 can then be closed, such as to allow the pump 150 to build positive gauge pressure in the apparatus 100.

At 1012, a sensor 130, such as a pressure sensor located in the cavity 112, can sense the fluid pressure in the cavity 112, such as for an indication of therapeutic fluid gauge pressure. The processor module 140 can receive a signal from the sensor 130, such as an electrical signal proportional to the gauge pressure of the therapeutic fluid. The received sensor signal can be compared to a predetermined set point value, such as a physician-recommended gauge pressure of the therapeutic fluid for the treatment of an eye condition, with the control circuit. If the received sensor signal is less than the predetermined gauge pressure set point value, the speed of the fan 153 can be increased at 711, such as to increase the volumetric fluid flow in the mixing chamber 146, and the therapeutic fluid can be re-sensed at 1013. The pump 150 can continue to generate volumetric fluid flow until the gauge pressure, such as sensed in the cavity 112, reaches the predetermined gauge pressure set point value.

At 1014, the pump can be stopped, such as upon achieving the predetermined gauge pressure set point value. Stopping the pump 150 can prevent changes in composition of the therapeutic fluid, such as in medicinal fluid concentration and gauge pressure.

At 1016, the valve in the fluid regulator 120C can be closed. Closing the valve of the fluid regulator 120C can stop the medicinal fluid from flowing out of the fluid source 170. In an example, the valve can be closed at a predetermined rate, such as a rate selected to prevent concentration changes in the therapeutic fluid.

At 1018, the sensor 130 can sense an indication of the therapeutic fluid in the cavity 112, such as for deviation from a specified set point value. In an example, an indication of the concentration of medicinal fluid in the therapeutic fluid can be sensed by the gas sensor and compared to the physician-recommended concentration set point level with the control circuit, such as to a tolerance range (or error band) centered around the set point level. In an example, an indication of the positive gauge pressure of the therapeutic fluid can be sensed by the pressure sensor and compared to the physician-recommended positive gauge pressure set point level with the control circuit, such as to a tolerance range (or error band) centered around the set point level. When the sensed indication falls outside the tolerance range, the method of 1000 can be reinitiated, such as at 1004, to adjust the sensed indication to a value within the tolerance range.

Figure 11:
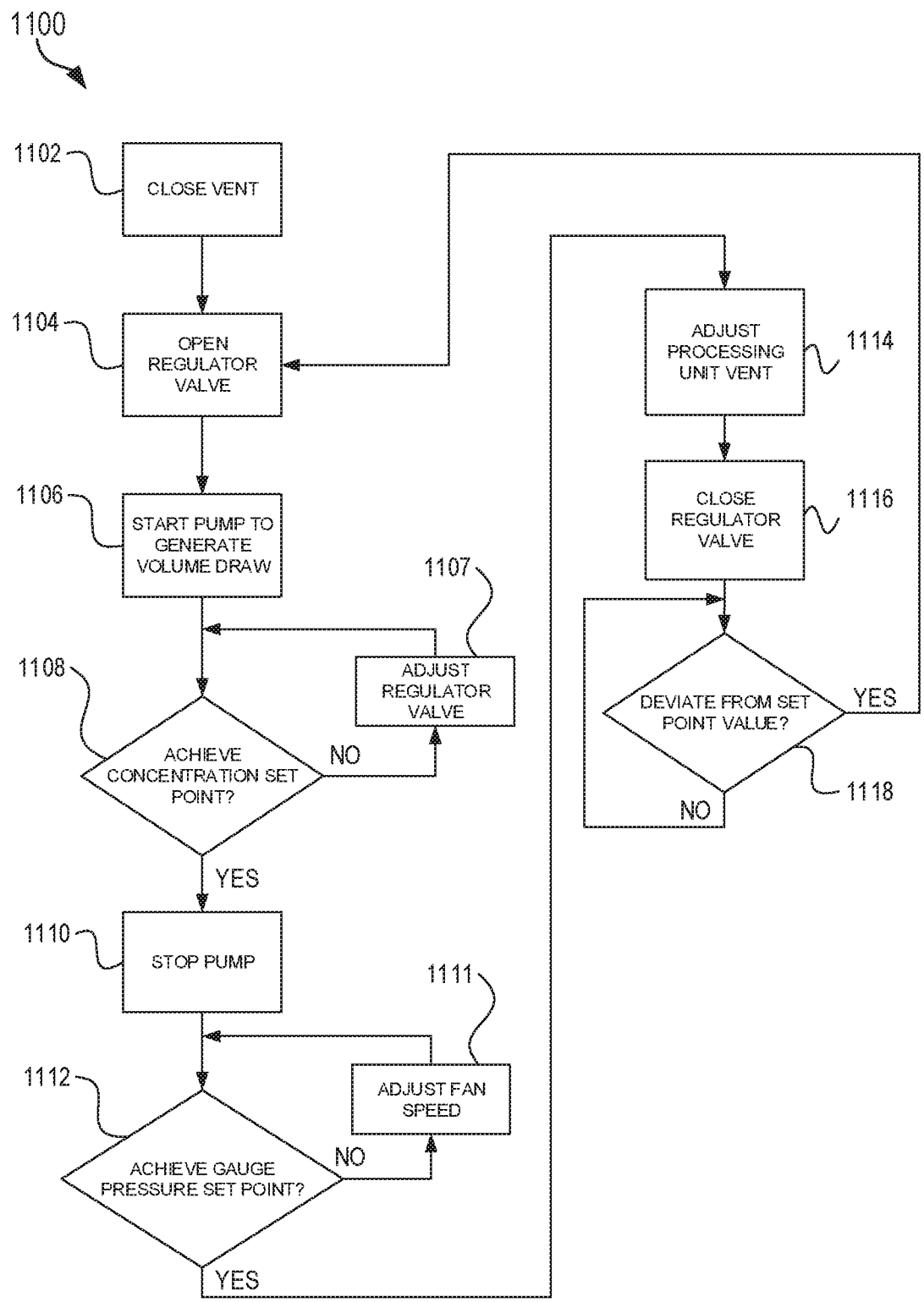
FIG. 11 shows an example method to introduce gaseous fluids into the cavity with a negative gauge pressure.

FIG. 11 shows an example method 1100 to introduce gaseous fluids, such as gaseous fluids other than ambient air, into the cavity 112 with a negative gauge pressure. In an example, a user can interact with the operations unit of the processor module 140, such as to initiate operation of the method 1100.

At 1102, the vent 144 can be closed. Closing the vent 144 can isolate fluid pressure in the apparatus 100, such as in the cavity 112, from the surrounding environment. Isolating pressure can prepare the cavity 112 to receive a mixture of gases other than ambient air, such as a mixture of therapeutic gases.

At 1104, the fluid regulator 120, such as the valve of the fluid regulator 120C, can be opened. Opening the valve of the fluid regulator 120C can allow a fluid, such as a medicinal fluid, to flow out of the fluid source 170 into the processor module 140, such as into the mixing chamber 146 in communication with the pressure tube 117. In an example, the composition of the therapeutic fluid can be adjusted, such as by changing the outflow rate of the fluid source, such as by opening and closing the valve of the fluid regulator 120C. In an example, the valve can be opened at a predetermined rate, such as to gradually increase the concentration of medicinal fluid released into the mixing chamber 146 over time.

At 1106, the pump 150 can be started to generate a volume draw, such as to generate a negative gauge pressure at the pump inlet 156. In an example, the pump outlet 155 can be blocked, and the pump inlet 156 can communicate indirectly with the mixing chamber 146, such as the pump inlet 156 can be in communication with the mixing chamber 146 through the pressure tube 117. For example, as the pump 150 generates a negative gauge pressure at the pump inlet 156, fluids in the mixing chamber 146, such as medicinal fluids, can be drawn through the pressure tube 117, such as through the pressure tube 117A into the cavity 112A, through the pressure tube 117O into the cavity 112B, and through the pressure tube 117B into the pump inlet 156. In drawing the medicinal fluid from the mixing chamber 146, the medicinal fluid can combine and mix with fluids in the cavity 112 and the pressure tube 117, such as to create a therapeutic fluid. The composition of the therapeutic fluid can depend on the volume draw of the pump 150 and on the volume and concentration of the medicinal fluid flowing through the fluid regulator 120C. In an example, the composition of the therapeutic fluid can be adjusted, such as by changing the volume draw of the pump 150. For example, the volume draw of the pump 150 can be changed by increasing or decreasing the speed of the pump 150, such as a centrifugal pump.

At 1108, a sensor 130, such as a gas sensor located in the cavity 112, can sense the therapeutic fluid flowing through the cavity 112, such as to sense an indication of the concentration of medicinal fluid in the therapeutic fluid. The processor module 140 can receive a signal from the sensor 130, such as an electrical signal proportional to the indication of the concentration of medicinal fluid in the therapeutic fluid. The received sensor signal can be compared to a predetermined set point value, such as a physician-recommended concentration of medicinal fluid for the treatment of an eye condition, with the control circuit. If the received sensor signal is less than the predetermined concentration set point value, the valve of the fluid regulator 120C can be further opened at 1107, such as to increase the concentration of medicinal fluid in the mixing chamber 146, and the therapeutic fluid can be re-sensed at 1108. The valve of the fluid regulator 120C can continue to open until the received sensor signal, such as sensed in the cavity 112, reaches the predetermined concentration set point value.

At 1110, the pump 150 can be stopped. After the received sensor signal meets the pre-determined set point value, the therapeutic fluid can be considered adequately mixed in the apparatus 100 at the negative gauge pressure in the cavity 112. The pump 150 can then be stopped, such as to maintain the negative gauge pressure in the apparatus 100.

At 1112, a sensor 130, such as a pressure sensor located in the cavity 112, can sense the fluid pressure in the cavity 112, such as for an indication of therapeutic fluid gauge pressure. The processor module 140 can receive a signal from the sensor 130, such as an electrical signal proportional to the gauge pressure of the therapeutic fluid. The received sensor signal can be compared to a predetermined set point value, such as a physician-recommended negative gauge pressure of therapeutic fluid for the treatment of an eye condition, with the control circuit. If the received sensor signal is greater than the predetermined gauge pressure set point value, the speed of the fan 153 can be increased at 1111, such as to increase the volumetric fluid draw in the mixing chamber 146, and the therapeutic fluid can be re-sensed at 1113. The pump 150 can continue to generate volumetric fluid draw until the gauge pressure, such as sensed in the cavity 112, reaches the predetermined gauge pressure set point value. In an example, the gauge pressure in the apparatus 100 can exceed the physician-recommended negative gauge pressure, such as the negative gauge pressure in the cavity 112 can be less than the physician-recommended negative gauge pressure.

At 1114, the vent 144 can be adjusted. Adjusting the vent 144 can allow air from the surrounding environment to be drawn into the apparatus 100, such as to reduce the negative gauge pressure in the cavity 112. In an example, the vent 144 can be adjusted by a predetermined method, such as to reduce the negative gauge pressure in the cavity 112 to within a specified error band of the negative gauge pressure set point value, such as a physician-recommended negative gauge pressure.

At 1116, the valve of the fluid regulator 120C can be closed. Closing the fluid regulator 120C can stop the medicinal fluid from flowing out of the fluid source 170. In an example, the valve can be closed at a predetermined rate, such as a rate selected to prevent concentration changes in the therapeutic fluid.

At 1118, the sensor 130 can sense an indication of the therapeutic fluid in the cavity 112, such as for a deviation from a specified set point value. In an example, an indication of the concentration of medicinal fluid in the therapeutic fluid can be sensed by the gas sensor and compared to the physician-recommended concentration set point level with the control circuit, such as to a tolerance range (or error band) centered around the set point level. In an example, an indication of the negative gauge pressure of the therapeutic fluid can be sensed by the pressure sensor and compared to the physician-recommended negative gauge pressure set point level with the control circuit, such as to a tolerance range (or error band) centered around the set point level. When the sensed indication falls outside the tolerance range, the method of 1100 can be reinitiated, such as at 1104, to adjust the sensed indication to a value within the tolerance range.

Figure 12:
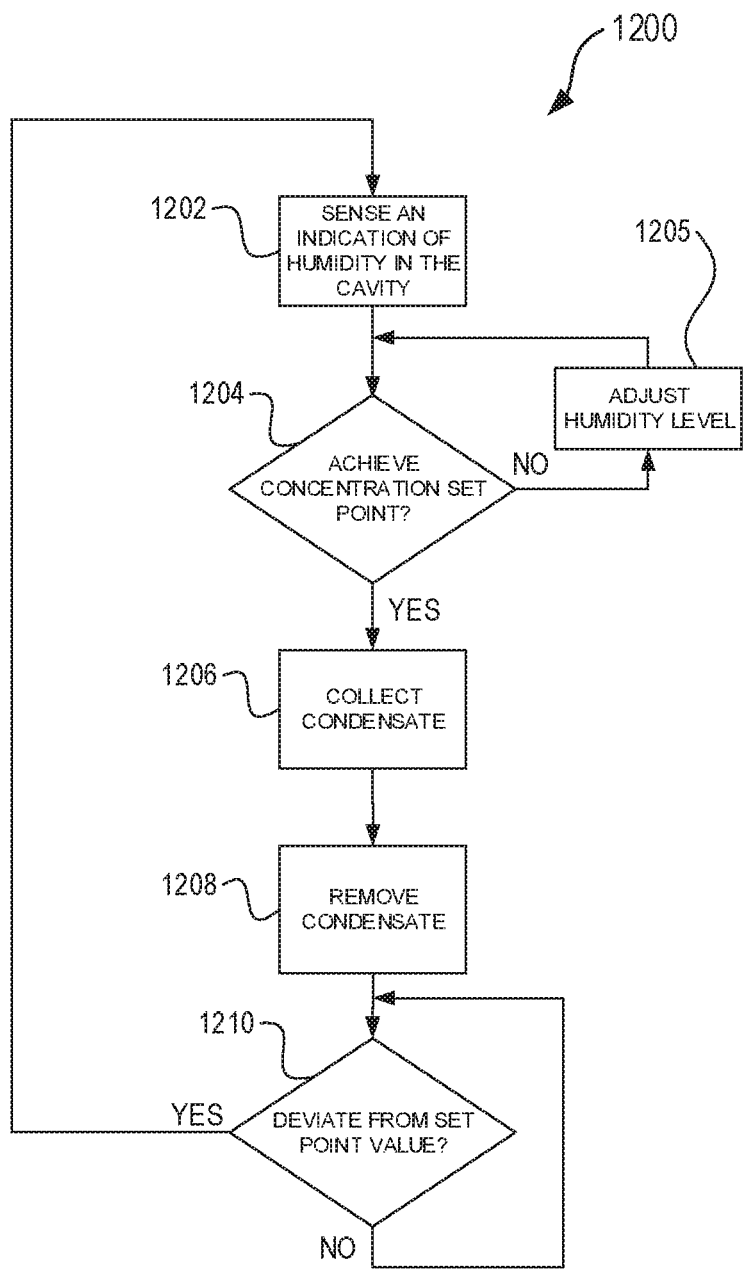
FIG. 12 shows an example method to control the level of water vapor in the cavity.

FIG. 12 shows an example method 1200 to control the level of water vapor (i.e. humidity) in the cavity 112, such as the level of humidity entrained in a therapeutic fluid. Maintaining physician-recommended humidity levels can enhance the effect of therapeutic fluids in contact with the eye. However, condensate can form in the cavity 112, such as due to the accumulation of perspiration. Control of humidity levels can impede the formation of condensate while improving treatment efficacy and patient comfort during use of the apparatus 100.

At 1202, a sensor 130, such as a humidity sensor located in the cavity 112, can sense an indication of the humidity level in the therapeutic fluid.

At 1204, the indication of the humidity level in the cavity 112 can be compared to a set point value, such as to determine if a humidity level has been achieved. In an example, the processor module 140 can receive a signal from the sensor 130, such as an electrical signal proportional to the indication of the humidity level in the therapeutic fluid. The received sensor signal can be compared to a predetermined set point value, such as a specified humidity level for the treatment of an eye condition, with the control circuit.

At 1205, the humidity level in the therapeutic fluid can be adjusted. If the received sensor signal is less than the humidity level set point value, the valve of a fluid regulator 120 can be opened, such as to increase the concentration of water vapor in the mixing chamber 146 available for mixing into the therapeutic fluid, and the therapeutic fluid can be re-sensed and compared to the set point value at 904. The valve of the fluid regulator 120 can continue to open until the received sensor signal reaches the predetermined humidity level set point value. If the received sensor signal is greater than the humidity level set point value, a filter 158, such as a desiccant filter, can be exposed to the therapeutic fluid, such as to at least a portion of the therapeutic fluid in the passage 157, to collect and remove excess water vapor.

At 1206, water vapor, such as water vapor entrained in the therapeutic fluid and accumulated condensate, can be collected from the apparatus 100. Therapeutic fluid flowing through the passage 157, such as by operating the fan 153 to circulate therapeutic fluid in the apparatus 100, can be exposed to, such as can come in contact with, at least a portion of the desiccant filter, such as to collect water vapor from the apparatus 100. The amount of therapeutic fluid exposed to the desiccant filter can be controlled by a slide valve, such as slide valve covering the desiccant filter and in communication with the control circuit of the processing module 140. The control circuit can adjust the slide valve, such as to adjust the surface area of the desiccant filter exposed to the therapeutic fluid, to control the rate at which water vapor can be extracted from the therapeutic fluid.

Accumulated condensate, such as in the cavity 112, can be collected, such as with a wicking gasket 160. Condensate can come into contact with the wicking core 162, such as a first surface 163 of the wicking core 162, for absorption by the wicking core 162. Absorbed condensate can distribute through the wicking core 162, such as by osmosis, and can be retained within the wicking core 162.

At 1208, collected water vapor can be removed from the apparatus 100. In an example, the desiccant filter, such as a desiccant filter saturated with water vapor, can be replaced in the pump 150, such as with a dry desiccant filter, to remove water vapor from the apparatus 100. In an example, the desiccant filter can be exposed to the ambient atmosphere, such as to allow water vapor to evaporate from the desiccant. In an example, the desiccant filter can include a heater element, such as integrated into a desiccant filter, to increase the temperature of the desiccant filter causing the collected water vapor to evaporate, such as into the ambient atmosphere.

Accumulated condensate, such as condensate retained within the wicking core 162, can be removed from the apparatus 100. In an example, condensate can migrate through the core cover 166, such as from the interior surface 167 to the exterior surface 168, and evaporate from the exterior surface 168, such as to remove condensate from the apparatus 100. In an example, a negative gauge pressure can be generated in the lumen of the suction tube 169, such as to draw condensate retained in the wicking core 162 to the suction tube 169. The negative gauge pressure can be generated by a condensate pump including a pump separate from the apparatus 100, such as a standalone vacuum pump that can be in communication with the control circuit of the processing module 140, and a pump included in the apparatus 100, such as the pump 150.

At 1210, the sensor 130 can sense an indication of the therapeutic fluid in the cavity 112, such as for deviation from a specified set point value. In an example, an indication of the humidity in the therapeutic fluid can be sensed by the humidity sensor and compared to the physician-recommended humidity set point level with the control circuit, such as to a tolerance range (or error band) centered around the set point level. When the sensed indication falls outside the tolerance range, the method of 1200 can be reinitiated, such as at 1202, to adjust the sensed indication to a value within the tolerance range.

VARIOUS NOTES & EXAMPLES

The above detailed description includes references to the accompanying drawings, which form a part of the detailed description. The drawings show, by way of illustration, specific embodiments in which the invention can be practiced. These embodiments are also referred to herein as "examples," Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein," Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the The claimed invention is:

1. An apparatus to maintain an environment over an anterior surface of a patient eye comprising:
    an enclosure sized and shaped to form a cavity over the anterior surface of the patient eye, the cavity configured to contain a fluid other than ambient air in contact with the patient eye;
    a fluid regulator, in communication with the cavity, configured to regulate the composition of the fluid contained within the cavity;
    a manifold including a mixing chamber, in communication with the fluid regulator and the cavity, configured to adjust the composition of the fluid contained within the cavity, and a pump in communication with the cavity, configured to apply non-ambient pressure to the fluid contained within the cavity.

2. The apparatus of claim 1, wherein the fluid is a gaseous fluid.

3. The apparatus of claim 2, wherein the gaseous fluid includes a specified non-ambient percentage of at least one of carbon dioxide ($CO_2$), oxygen ($O_2$), or nitric oxide (NO).

4. The apparatus of claim 3, wherein the gaseous fluid includes a specified non-ambient percentage of carbon dioxide ($CO_2$).

5. The apparatus of claim 3, wherein the gaseous fluid includes a specified non-ambient percentage of oxygen ($O_2$).

6. The apparatus of claim 3, wherein the gaseous fluid includes a specified non-ambient percentage of nitric oxide (NO).

7. The apparatus of claim 1, comprising a processor module including a control circuit with a user-defined set point, in communication with the fluid regulator; and
    a sensor, in communication with the processor module, configured to sense at least one of an indication of the eye or an indication of a parameter of an environment within the cavity,
    wherein the fluid regulator includes a servo valve and the control circuit is configured to adjust the servo valve to change the composition of the fluid contained within the cavity.

8. The apparatus of claim 7 wherein the sensor configured to detect at least one of an indication of the eye or an indication of a parameter of an environment within the cavity includes the sensor configured to detect an indication of the eye.

9. The apparatus of claim 8, wherein the sensor configured to detect an indication of the eye includes an optical coherence tomography (OCT) system configured to sense a change in the deflection of the lamina cribrosa.

10. The apparatus of claim 8, wherein the sensor configured to detect an indication of the eye includes a non-contact blood vessel characteristic detector configured to sense a change in the caliber of a blood vessel.

11. The apparatus of claim 7, wherein the sensor configured to detect at least one of an indication of the eye or an indication of a parameter of an environment within the cavity includes the sensor configured to detect an indication of a parameter of an environment within the cavity.

12. The apparatus of claim 11, wherein the sensor configured to detect an indication of a parameter of an environment within the cavity includes a non-invasive optical oxygen sensor configured to sense an indication of oxygen level within the cavity.

13. The apparatus of claim 1, wherein the pump to apply non-ambient pressure to the fluid contained within the cavity includes the pump configured to apply negative gauge pressure to the cavity.

14. The apparatus of claim 13, wherein the pump configured to apply negative gauge pressure to the cavity includes the pump configured to apply negative gauge pressure to the cavity in a range of between about −40 mmHg and about 0 mmHg.

15. The apparatus of claim 1, wherein the pump to apply non-ambient pressure to the fluid contained within the cavity includes the pump configured to apply positive gauge pressure to the cavity.

* * * * *